(12) United States Patent
Nagar

(10) Patent No.: US 12,398,937 B2
(45) Date of Patent: Aug. 26, 2025

(54) DEVICES, SYSTEMS AND METHODS FOR CONTROLLING ENVIRONMENTAL CONDITIONS OF SUBSTANCES

(71) Applicant: Ron Nagar, Tel Aviv (IL)

(72) Inventor: Ron Nagar, Tel Aviv (IL)

( * ) Notice: Subject to any disclaimer, the term of this patent is extended or adjusted under 35 U.S.C. 154(b) by 4 days.

(21) Appl. No.: 17/288,497

(22) PCT Filed: Oct. 24, 2019

(86) PCT No.: PCT/IB2019/059096
§ 371 (c)(1),
(2) Date: Apr. 23, 2021

(87) PCT Pub. No.: WO2020/084543
PCT Pub. Date: Apr. 30, 2020

(65) Prior Publication Data
US 2021/0396446 A1 Dec. 23, 2021

Related U.S. Application Data

(60) Provisional application No. 62/790,485, filed on Jan. 10, 2019, provisional application No. 62/749,769, filed on Oct. 24, 2018.

(51) Int. Cl.
*F25D 3/08* (2006.01)
*A61J 1/16* (2023.01)
*F25D 31/00* (2006.01)

(52) U.S. Cl.
CPC ............... *F25D 3/08* (2013.01); *A61J 1/165* (2013.01); *F25D 31/005* (2013.01); *F25D 2303/0843* (2013.01); *F25D 2303/085* (2013.01)

(58) Field of Classification Search
CPC .. A61J 1/165; A61J 2007/108; A61J 2200/44; F25D 2331/801;
(Continued)

(56) References Cited

U.S. PATENT DOCUMENTS 3,802,220 A * 4/1974 Pompo ...................... F25D 3/00
62/457.2
3,893,834 A * 7/1975 Armstrong ............ A61M 5/002
607/114

(Continued)

FOREIGN PATENT DOCUMENTS

CN 101208568 A 6/2008
CN 108027192 A 5/2018
(Continued)

OTHER PUBLICATIONS

Machine English Translation of FR 2635580 to Guillon. Translated Oct. 2023 (Year: 1900).*

(Continued)

*Primary Examiner* — Cassey D Bauer
(74) *Attorney, Agent, or Firm* — Fenwick & West LLP

(57) ABSTRACT

An environmental control assembly for controlling at least one environmental condition of one or more substances, the one or more substances being uncontained or contained within a substance container, the assembly comprising a first enclosure comprising a thermal insulator configured to provide a thermal shield to the substance, a second enclosure comprising at least one deformable environmental control material configured to regulate at least one environmental condition of the substance, wherein the second enclosure at least partially physically contacts with at least one of the substance and the substance container, and a housing at least partially comprising the first enclosure and the second enclosure.

29 Claims, 11 Drawing Sheets

(58) Field of Classification Search
CPC ..... F25D 2331/8012; F25D 2303/0822; F25D 31/005; F25D 2303/0843; F25D 2303/085; F25D 2331/8014; F25D 5/02; F25D 3/08; B65D 81/052; B65D 81/1075; A61F 7/106; A61F 2007/108

See application file for complete search history.

(56) References Cited

U.S. PATENT DOCUMENTS

| | | | |
|---|---|---|---|
| 4,373,535 | A | 2/1983 | Martell |
| 4,619,678 | A * | 10/1986 | Rubin ................... A61J 1/165 62/457.2 |
| 4,723,974 | A | 2/1988 | Ammerman |
| 4,924,935 | A | 5/1990 | Van Winckel |
| 5,603,220 | A | 2/1997 | Seaman |
| 5,695,090 | A | 12/1997 | Burdick |
| 6,454,746 | B1 | 9/2002 | Bydlon et al. |
| 7,240,513 | B1 | 7/2007 | Conforti |
| 7,861,538 | B2 | 1/2011 | Welle et al. |
| 8,061,149 | B1 | 11/2011 | Gowans et al. |
| 8,398,602 | B2 | 3/2013 | Ilo et al. |
| 8,646,282 | B2 | 2/2014 | Ilercil et al. |
| 8,663,167 | B2 | 3/2014 | Bartha |
| 8,887,512 | B2 | 11/2014 | Olsen et al. |
| 9,447,995 | B2 | 9/2016 | Bloedow et al. |
| 9,581,384 | B1 | 2/2017 | Scofield et al. |
| 9,791,184 | B2 | 10/2017 | Novisoff et al. |
| 10,254,499 | B1 | 4/2019 | Cohen et al. |
| 10,973,996 | B2 | 4/2021 | Nagar |
| 11,499,770 | B2 * | 11/2022 | Rizzo ................... F25D 11/003 |
| 11,857,495 | B2 | 1/2024 | Nagar |
| 11,992,459 | B2 | 5/2024 | Nagar |
| 2001/0048985 | A1 | 12/2001 | Legare |
| 2002/0000443 | A1 | 1/2002 | Hunter |
| 2003/0128898 | A1 * | 7/2003 | Malone ................... F25D 3/08 383/3 |
| 2006/0191282 | A1 | 8/2006 | Sekiya et al. |
| 2006/0271014 | A1 | 11/2006 | Hynes et al. |
| 2006/0276768 | A1 | 12/2006 | Miller et al. |
| 2008/0022696 | A1 | 1/2008 | Welle et al. |
| 2008/0264261 | A1 | 10/2008 | Kavazov et al. |
| 2008/0269687 | A1 | 10/2008 | Chong et al. |
| 2009/0049845 | A1 * | 2/2009 | McStravick ........... A61M 5/003 62/3.62 |
| 2009/0139248 | A1 | 6/2009 | Crumlin et al. |
| 2009/0301511 | A1 | 12/2009 | Vinci |
| 2010/0314397 | A1 * | 12/2010 | Williams ........... B65D 81/3823 220/592.01 |
| 2011/0155621 | A1 | 6/2011 | Lindquist et al. |
| 2011/0218502 | A1 | 9/2011 | Iio et al. |
| 2012/0312031 | A1 | 12/2012 | Olsen et al. |
| 2013/0221013 | A1 | 8/2013 | Kolowich et al. |
| 2013/0255306 | A1 | 10/2013 | Mayer |
| 2014/0090737 | A1 | 4/2014 | Reid |
| 2014/0165607 | A1 | 6/2014 | Alexander |
| 2014/0216485 | A1 | 8/2014 | Egoyants et al. |
| 2014/0263368 | A1 | 9/2014 | Booska |
| 2014/0343493 | A1 | 11/2014 | Wengreen |
| 2015/0151893 | A1 | 6/2015 | Wengreen et al. |
| 2015/0229267 | A1 | 8/2015 | Hilliard |
| 2015/0239640 | A1 * | 8/2015 | Smith ................... B65D 43/162 220/592.2 |
| 2016/0311585 | A1 | 10/2016 | Rideg |
| 2017/0241702 | A1 | 8/2017 | Klett et al. |
| 2018/0036202 | A1 | 2/2018 | Wengreen et al. |
| 2018/0207368 | A1 | 7/2018 | Nagar |
| 2018/0283761 | A1 | 10/2018 | Büttiker |
| 2018/0328644 | A1 * | 11/2018 | Rizzo ................... F25D 11/003 |
| 2018/0333330 | A1 | 11/2018 | Nagar |
| 2019/0226744 | A1 * | 7/2019 | Wood ................... F25D 3/08 |
| 2019/0285328 | A1 | 9/2019 | Emond et al. |
| 2020/0171291 | A1 | 6/2020 | Snyder |
| 2021/0228820 | A1 | 7/2021 | Nagar |
| 2024/0342057 | A1 | 10/2024 | Nagar |
| 2025/0090422 | A1 | 3/2025 | Nagar |

FOREIGN PATENT DOCUMENTS

| | | | |
|---|---|---|---|
| CN | 209209482 U | 8/2019 | |
| EP | 2361203 A1 | 8/2011 | |
| EP | 3610842 A1 | 2/2020 | |
| FR | 2635580 * | 8/1988 | .............. A61J 1/165 |
| GB | 2176711 A | 1/1987 | |
| GB | 2422657 A | 8/2006 | |
| JP | 02115672 A | 4/1990 | |
| JP | 04201877 A | 7/1992 | |
| JP | 3041860 U | 10/1997 | |
| WO | WO-9930092 A1 | 6/1999 | |
| WO | WO-2013034458 A1 | 3/2013 | |
| WO | WO-2014064691 A2 | 5/2014 | |
| WO | WO-2014163120 A1 | 10/2014 | |
| WO | WO-2014192019 A2 | 12/2014 | |
| WO | WO-2015055836 A1 | 4/2015 | |
| WO | WO-2015093311 A1 | 6/2015 | |
| WO | WO-2016011207 A1 | 1/2016 | |
| WO | WO-2017090019 A2 | 6/2017 | |
| WO | WO-2020084543 A1 | 4/2020 | |

OTHER PUBLICATIONS

Extended European Search Report for Application No. EP 19875793.2, mailed on Oct. 14, 2022, 11 pages.

Extended European Search Report issued on Feb. 21, 2018, for EP Application No. 15822617.5, 7 pages.

Extended European Search Report issued on Jul. 2, 2019, for EP Application No. 16868134.4, 7 pages.

Extended European Search Report issued on Nov. 20, 2019, for EP Application No. 19181060.5, 7 pages.

International Search Report and Written Opinion, mailed Oct. 7, 2015, for International Application No. PCT/US2015/040655, 15 pages.

International Search report for Application No. PCT/IL16/00021, dated May 16, 2017, 4 pages.

International Search Report issued in PCT/IB2019/059096, dated Feb. 4, 2020, 3 pages.

Screenshots from Website: www.insulinsafe.com.cn/en/; May 10, 2013; Beijing Insulinsafe Healthcare Limited, 1 page.

Screenshots from Website: www.insulinsafe.com.cn/en/category/product; Sep. 13, 2014; Beijing Science and Technology Co., Ltd., 11 pages.

International Search Report and Written Opinion for International Application No. PCT/IB2022/00051, dated Jun. 30, 2022, 20 pages.

European Search Report for Application No. 24194202.8 dated Feb. 28, 2025, 12 pages.

Extended European Search Report for European Application No. 22749297.2 mailed Dec. 13, 2024, 9 pages.

\* cited by examiner

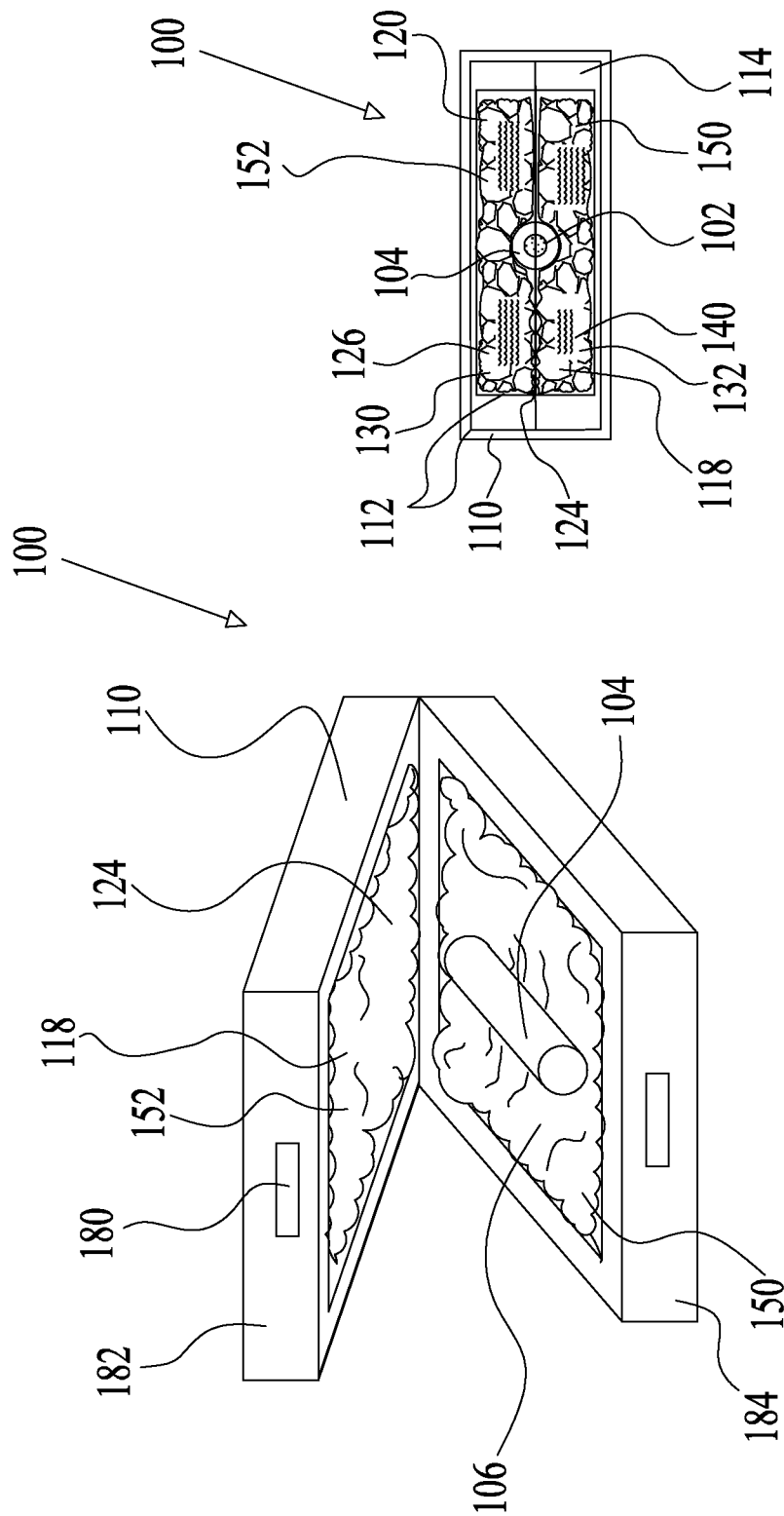

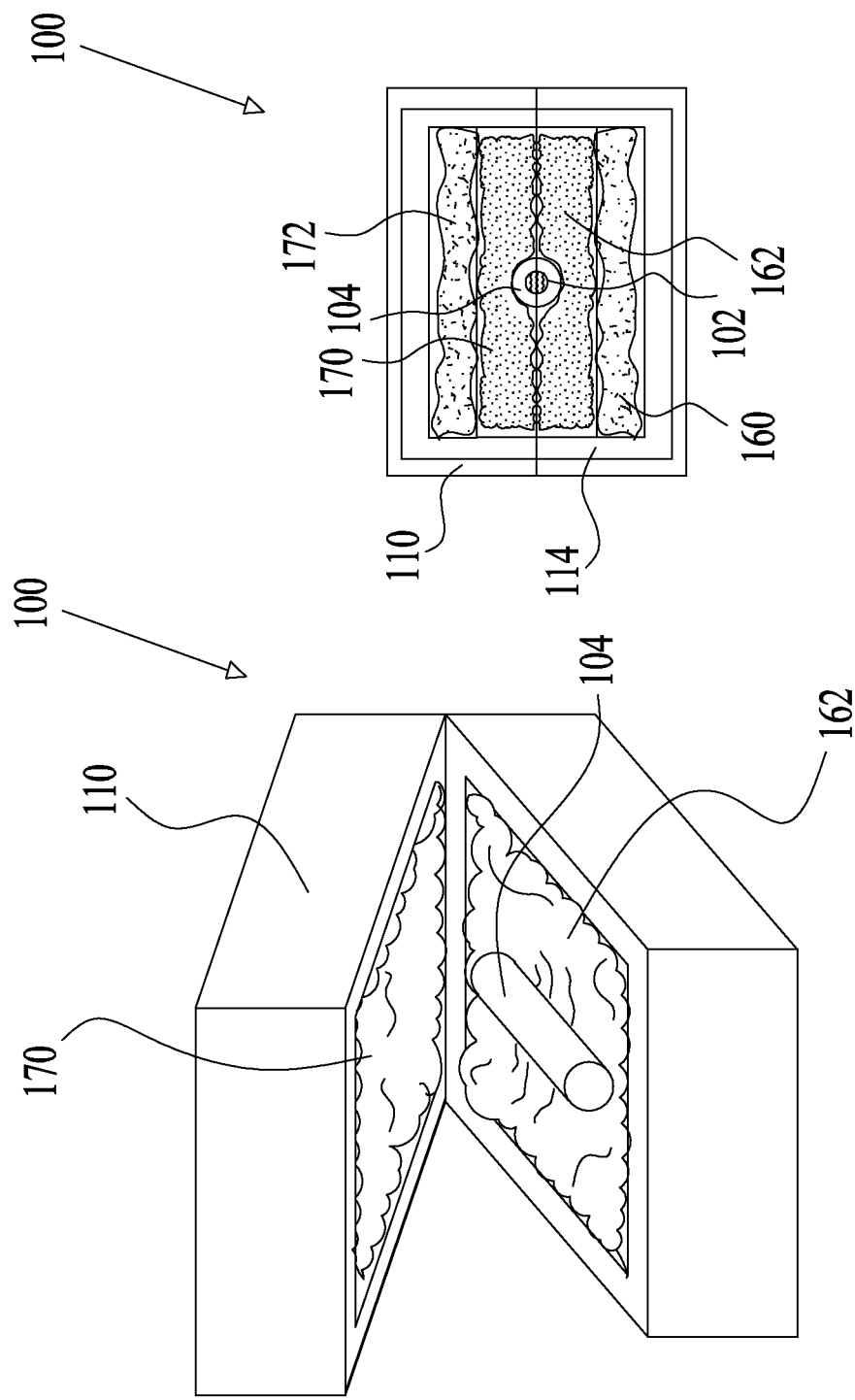

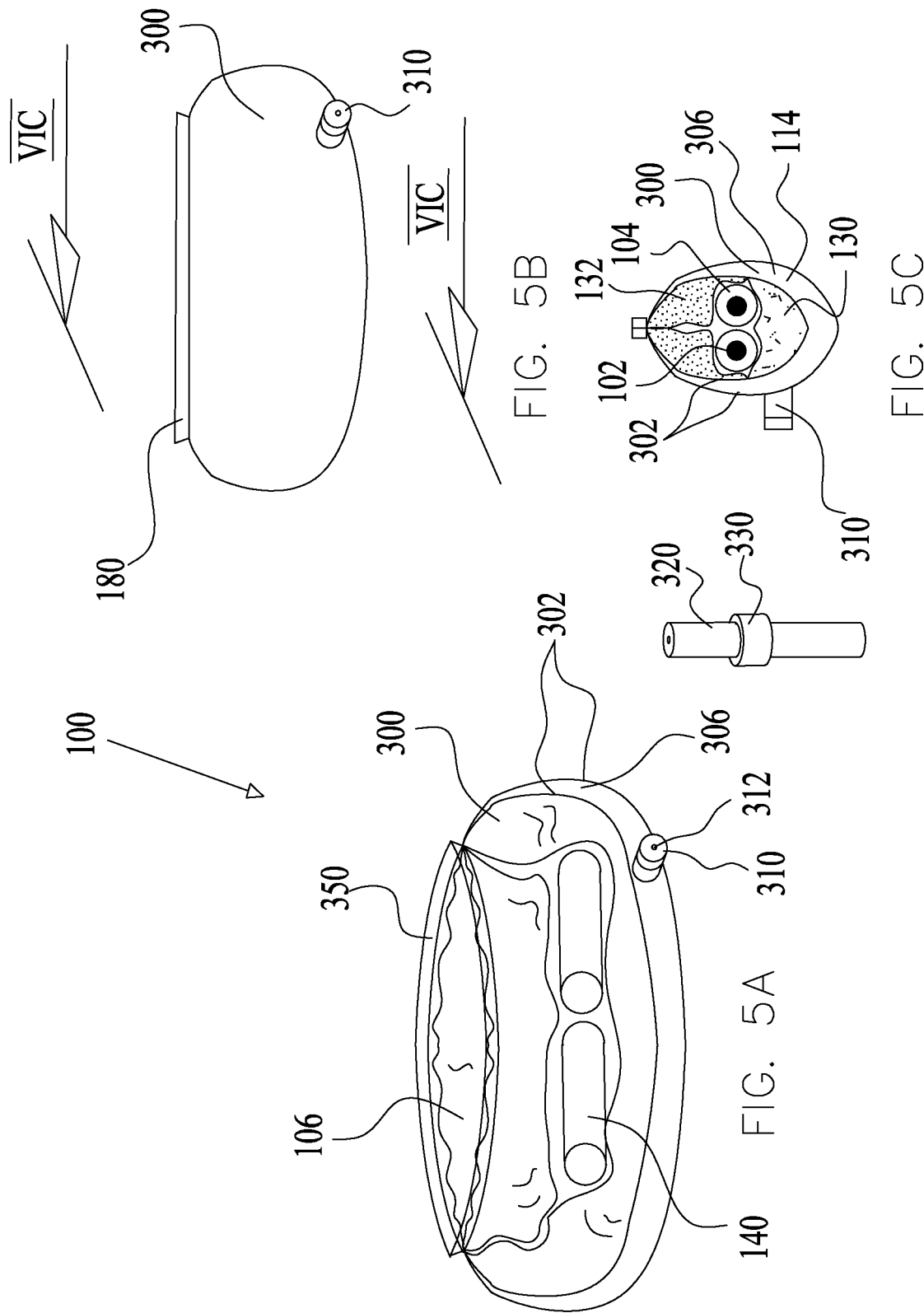

DEVICES, SYSTEMS AND METHODS FOR CONTROLLING ENVIRONMENTAL CONDITIONS OF SUBSTANCES

RELATED APPLICATIONS

This application claims benefit of and priority to U.S. Provisional Patent Application No. 62/749,769, filed Oct. 24, 2018, titled: "Devices, Systems and Methods for Controlling and Maintaining Conditions of Substances" and U.S. Provisional Patent Application No. 62/790,485, filed Jan. 10, 2019, titled "Devices, Systems and Methods for Controlling and Maintaining Conditions of Substances". Each of the foregoing disclosures are herein incorporated by reference in their entirety.

TECHNICAL FIELD

Some embodiments of the present disclosure generally relate to the targeted controlling of substance environmental conditions.

BACKGROUND

Drugs and other substances can be sensitive to environmental conditions such as light, humidity, temperature, atmosphere, pressure and other conditions. Many drugs and other substances have limited boundaries to such conditions that if exceeded, can degrade the drug efficacy or degrade the substance.

Additionally, users receive drugs at the pharmacy and must carry these drugs to their home. When these drugs have to be kept refrigerated, users have trouble making sure that the volume of drug is refrigerated during transport to their domestic refrigerator. While they use icepacks, these icepacks do not come in contact with the drug and as a result do not assure that the drug is at proper refrigeration temperature. In some cases, should the ice packs make direct contact with the drug it might freeze, causing the drug to degrade.

While apparatuses exist that can maintain drugs and substance containers, such as drug-containing delivery devices, under controlled environmental conditions, such current apparatuses are quite large and typically require a regular AC power supply for their operation, or large batteries of limited duration. Other devices, such as cooling packs, require large amounts of cooling material (ice or water evaporation) to maintain a case under cooled temperatures.

To date there is no simple, inexpensive device for maintaining drugs and other temperature sensitive substances at refrigeration temperatures (e.g. 0-8° C. or 2-8° C.) or at any other desired temperature, that is portable and does not require the user to perform an unordinary activity in order for the device to keep providing the controlled conditions for time periods of hours, days, weeks and even years, without need for the user to use external electrical power or other special unordinary activity to specially "charge" the device. Specifically, there is a need for maintaining substance temperatures stored in domestic refrigerators during power outages. Furthermore, there is a need for ensuring the substances do not freeze while being stored in domestic or any other type of refrigeration. Moreover, there is a need for a transporting apparatus used for maintaining a desired substance temperature when transporting the substance from the pharmacy to the home/domestic refrigerator and/or any time the substance is out of a refrigerator. While assuring that substantially under all such circumstances the substances, that can be either contained in one or more containers or uncontained, will be maintained at the desired, predetermined temperature within a predetermined temperature range. In other words there is a need for a device configured such that the environmental conditions within the device are uniform.

SUMMARY OF SOME OF THE EMBODIMENTS

In some embodiments of the present disclosure, the environmental conditions of any substance may be controlled. The environmental condition (which may be referred to as "condition" herein) may include light, humidity, temperature, atmosphere, pressure or any other condition affecting the substance.

The substance may comprise any material affected by the condition. In a non-limiting example, the substance may comprise a drug, a pharmaceutical, a biological substance, such as hormones, a growth hormone, blood, enzymes, body fluids, body parts, body organs, body tissue, sperms, or eggs. The substance may comprise analyte indicators, analyte sensors and/or analyte detectors comprising any type of material. The analyte indicator or sensor may comprise for example, a blood glucose test strip or blood glucose sensitive materials, configured for indicating the blood glucose level. The blood glucose strip may comprise enzymes or any other biological material. In another example, the analyte indicator or sensor may comprise urine test strips. The analyte indicator or sensor may comprise any diagnostic tool based on a biological indicator comprising a biological and/or chemical material. The substance may comprise cosmetics, such as lipsticks, perfumes, toiletries, hair or skin care products, sprays, mousses, emulsions and gels, for example. The substance may comprise, resins, adhesives, glues, epoxy or cyanoacrylate glue, for example. The substance may include any suitable form, such as a solid, liquid, emulsion, gas, gel, granules, and powder or a combination thereof, for example. The substance may include more than one substance at the same or different state or phase, such as, for example, a liquid mixed with another liquid or a liquid mixed with a powder. In some embodiments, keeping one part of the mixture at a particular environmental condition requires a smaller amount of power than both parts. For example, a substance in a powder state is of smaller volume than the same substance in its liquid state. Therefore maintaining a small amount of powder at a specific temperature requires less power than maintaining larger amount of liquids at the specific temperature.

There is thus provided in accordance with an embodiment of the disclosure an environmental control assembly for controlling at least one environmental condition of one or more substances, the one or more substances being uncontained or contained within a substance container. The assembly includes a first enclosure including a thermal insulator configured to provide a thermal shield to the substance, a second enclosure including at least one deformable environmental control material configured to regulate at least one environmental condition of the substance. The second enclosure at least partially physically contacts with at least one of the substance and the substance container, and a housing at least partially includes the first enclosure and the second enclosure. In some embodiments, the environmental control material is thermally self-recharging. In some embodiments, the first enclosure at least partially encases the second enclosure. In some embodiments, the second enclosure forms a chamber configured to receive at least one of the substance and the substance container, and the second enclosure contiguously contacts at least one of the substance and the substance container so as to minimize air-pockets formed intermediate the deformable enclosure and at least one of the substance and the substance container.

In some embodiments, the second enclosure includes at least one compartment and wherein at least two types of environmental control materials are mixed together and placed in a single compartment. In some embodiments, the second enclosure includes a plurality of compartments and each compartment includes a single type of environmental control material. In some embodiments, a first compartment of the second enclosure includes a first type of environmental control material and a second compartment of the second enclosure includes a second, different type of environmental control material.

In some embodiments, the environmental control material includes at least one or more types of phase change materials (PCM). In some embodiments, a first type of PCM includes bulk PCM and a second type of PCM includes micro encapsulated PCM. In some embodiments, a type of environmental control material includes $H_2O$. In some embodiments, a first type of environmental control material includes a PCM and a second type of environmental control material includes $H_2O$. In some embodiments, the ratio of the PCM to $H_2O$ is in the range of about 1:1 to about 10:1 (PCM:$H_2O$).

In some embodiments, the environmental control material includes at least two types of environmental control materials, a first environmental control material of the at least two types of environmental control materials is configured with a high phase change temperature, and a second environmental control material of the at least two types of environmental control materials is configured with a low phase change temperature.

In some embodiments, a heating element is configured to heat the substance. In some embodiments, the heating element is configured to heat the substance while not exceeding a maximal temperature efficacy limit of the substance. In some embodiments, the assembly includes a power source. In some embodiments, the assembly includes a locking mechanism for closing the housing. In some embodiments, the assembly includes communication means for wired or wirelessly communicating with a remote device.

In some embodiments, the housing is formed of a rigid material. In some embodiments, the housing is formed of a flexible material.

In some embodiments, the first enclosure may include a selectively inflatable and/or deflatable closure configured to introduce air therein upon inflation thereof and remove the air therefrom upon deflation thereof. In some embodiments, the assembly is configured to be placed within a compartment of a refrigerator that is sized and constructed to house the assembly. In some embodiments, the assembly is configured to be removable from the refrigerator compartment.

In some embodiments, the assembly is configured for attachment and transport by a drone.

There is thus provided in accordance with an embodiment of the present disclosure, an environmental control system for controlling at least one environmental condition of one or more substances, the one or more substances being uncontained or contained within a substance container. The system includes the environmental control assembly and a portion wherein the environmental condition is uncontrolled. In some embodiments, system includes a refrigerator. In some embodiments, the system includes a drug infusion device.

There is thus provided in accordance with an embodiment of the present disclosure, an environmental control assembly for controlling at least one environmental condition of one or more substances, the one or more substances being uncontained or contained within a substance container, the assembly including a first enclosure including a thermal insulator configured to provide a thermal shield to the substance, at least one environmental control material configured to regulate the at least one environmental condition of the substance, a heat distributor configured for distributing heat along the substances and/or container, and a housing at least partially including the first enclosure.

There is thus provided in accordance with an embodiment of the present disclosure, a method for controlling at least one environmental condition of one or more substances, the one or more substances being uncontained or contained within a substance container, including thermally insulating the substance, and regulating the at least one environmental condition of the substance with a deformable environmental control material while at least partially physically contacting the at least one of the substance and the substance container with the deformable environmental control material.

It is noted that the environmental control assembly is mainly described in reference to a condition comprising temperature, it being appreciated that the disclosure is applicable to any type of condition.

In accordance with an embodiment of the present disclosure the environmental control assembly comprises a self recharging assembly. The self recharging assembly may comprise a PCM configured with a phase transition temperature selected such that during ordinary use of the assembly by the user (namely without requiring a user to perform any activity other than activity they do anyway when using the substance) there is enough time for at least a portion the PCM to become solid after exposure to extreme temperatures (relatively to the desired condition, that can also be high or low) which may otherwise degrade the substance. In a non-limiting example, an assembly containing a drug and comprising insulation and adequate amount of PCM with a transition temperature of 28° C. will be self recharging overnight. As the temperature gets below 28° C. it is enough for a user to return home for the PCM to at least partially "recharge" while during the day the assembly provides protection to preventing the drug from getting to temperature above 30° C., or any temperature which can degrade the drug, during the entire daylight time. The self recharging assembly is also configured to be placed in refrigeration, which in some embodiments is considered ordinary use and without "special" user intervention, since the typical use of some drugs (e.g. insulin) is to refrigerate the drug prior to use. Hence the self recharging assembly is configured to be used to maintain and control the environmental condition of the substance both in a refrigerated environment and in the outdoor environment or out of the refrigerator, without requiring the user to perform any unordinary intervention.

There is provided according to an embodiment, a thermally insulated apparatus having at least one or more insulated chambers or volumes. The thermally insulated apparatus may also be referred to as an "environmental condition control device" or as an "environmental condition control assembly". At least one of the thermally insulated chambers has a deformable surface configured to conform to the shape of (i) one or more or substance containing devices or containers (e.g. a drug injection device or any drug delivery device) or (ii) uncontained substances placed on the surface of one deformable surface. The substance containing devices or containers, the drug injection device or any drug delivery device, and the substances, uncontained or contained in a container may be collectively referred to as "substances and/or containers". The deformable surface conforms to the shape of the one or more substances and/or containers when the insulated chambers are closed against each other using a locking mechanism.

The deformation of the deformable surface allows placement of any one or more substances and/or containers, having the same, or different shapes, containing temperature sensitive substances. When the surfaces are closed against each other using a locking or sealing mechanism, thermal and physical (namely mechanical) contact is established between both deformable surfaces and the substances and/or containers. At least one insulated chamber comprises at least one type of bulk PCM or microencapsulated PCM and/or water.

Closing the chambers against each other minimizes air gaps between the at least one or more substances and/or containers and the deformable surfaces. This allows thermal conductivity between the environmental control material (e.g. bulk PCM and or microencapsulated PCM and/or water) and the temperature sensitive substances and/or containers, and maintains a temperature during a period of time within a specific, predetermined temperature limit or temperature range, without requiring electrical power to power the assembly.

In some embodiments, instead of a deformable surface a fan operates to achieve a uniform temperature inside the device. In some embodiments other means are used to achieve uniform temperature over or along the substances and/or the containers.

In accordance with some embodiments, the thermally insulated assembly may comprise an inflated and/or deflated air bag in at least one of the insulated chambers that can be inflated and deflated to adjust the thermal conductivity between the deformable surface and the substances and/or containers, when the two chambers are closed against each other and locked by the device locking mechanism.

In some embodiments, the inflated and/or deflated air bag may comprise an inflatable container, which may be shaped as a box or cylinder form or any other form. The inflatable container may include an insulated chamber for the substances and/or containers and a PCM or other environmental control material. The inflatable container may be configured to be opened to insert the substances and/or containers inside and inflate to insulate the PCM or deflate when it is desirable not to have insulation.

In accordance with some embodiments, the thermally insulated device comprises a thermally insulated chamber having walls that can be rigid or flexible or can be flat or structured to be inflatable. Inside the thermally insulated chamber there may be a volume of at least one thermal bank material (i.e. material with high thermal storage capacity, namely the environmental control material) enclosed in an enclosure which can be detachable or permanently fixed to the inner wall of the thermally insulating chamber or having several surfaces of the thermally insulating chamber enclosing the volume and another deformable/flexible surfaces enclosing the volume. The insulating chamber may have an opening or can be opened into two parts to place substances and/or containers on the deformable surface. The insulating chamber may be closed such that the substances and/or containers are in thermal contact, at least in part, with the deformable surface and the thermal bank. Between the substances and/or containers inside there may be optionally provided structure or means to minimize air to achieve uniform temperature along the temperature sensitive substances and/or containers. The device may optionally include electronics to control the temperature and optionally wirelessly communicate with a remote or external device.

In accordance with some embodiments, the thermally insulated assembly may include electronics and at least one temperature sensor to allow wireless communication of the temperature inside the assembly and additional parameters relating to the use of the assembly such as events of opening the assembly.

In accordance with some embodiments, a domestic refrigerator may be configured to comprise the insulated chamber. The insulated chamber may include PCM residing inside the insulated chamber and optionally an electrically powered thermoelectric element or both PCM and thermoelectric element, a temperature sensor which measures the temperature of the substances and/or containers and a controller. The thermoelectric element is activated in response to the substances and/or substance container measured temperature. This is to avoid the substances and/or containers from reaching a limit temperature or exceeding a temperature range. In a non-limiting example, the thermoelectric element may be used for heating the inner part of the chamber to avoid freezing. The refrigerator may include elements to detect presence of substances and/or containers and optionally the amount of the substance. This information, e.g. the amount, may be communicated to a user Smartphone or other external device or to a control unit of the refrigerator. The control unit may be configured to further communicate this information to a user Smartphone or other external device to provide wireless remote control of the substances and/or containers residing inside the insulated assembly.

There is provided a method for storing and carrying temperature sensitive substances wherein the user is not required to add auxiliary thermal storage elements (elements that have high heat capacity) before or during use of the thermally insulated assembly. There is provided a method for transporting temperature sensitive substances by drones wherein there is no need for the operators to insert thermal storage elements into a chamber used by the drone in order to carry the temperature sensitive substance. Rather the temperature of the temperature sensitive substances is controlled by the thermally insulated assembly (namely the environmental condition control assembly) with no need for auxiliary thermal storage elements.

The thermally insulated assembly may be placed inside a domestic refrigerator to set the temperature of the thermally insulated assemblies placed therein to refrigerated temperature while avoiding freezing of the substances and/or containers inside the thermally insulated assembly. The thermally insulated device can maintain a refrigerated temperature for hours even if the refrigerator does not work.

The thermally insulated device can further be carried by the user while maintaining refrigerated temperature, which in a non-limiting example may be 0°-8 C or 2°-8 C, for a predetermined duration (e.g. from a few minutes to 100 hours or more) without requiring the user to place ice packs or gel packs inside. In some embodiments, the thermally insulated device may be configured upon returning to the refrigerator, even after days in the outdoor environment, to regain the ability to maintain a refrigeration temperature and avoid freezing of the substances placed inside, without requiring the user to place the thermally insulated device in a freezer first or place ice packs or gel packs inside.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The principles and operations of the systems, apparatuses and methods according to some embodiments of the present disclosure may be better understood with reference to the drawings, and the following description. The drawings are given for illustrative purposes only and are not meant to be limiting.

FIGS. 1A-1C are a schematic illustration of an exemplary environmental condition control assembly at an open state (1A), a sectional view at a closed state (1B) and an exemplary environmental condition control assembly at an open state (1C) constructed and operative according to some embodiments of the present disclosure;

FIGS. 3A and 3B are a schematic illustration of an exemplary environmental condition control assembly at an open state (3A) and a sectional view at a closed state (3B) constructed and operative according to some embodiments of the present disclosure;

FIGS. 5A-5C are a schematic illustration of an exemplary environmental condition control assembly (5A) at an initial operational state, at a further operational state (5B) and a sectional view taken along lines VIC-VIC in FIG. 5B (5C), constructed and operative according to some embodiments of the present disclosure;

DETAILED DESCRIPTION

Figure 1C:
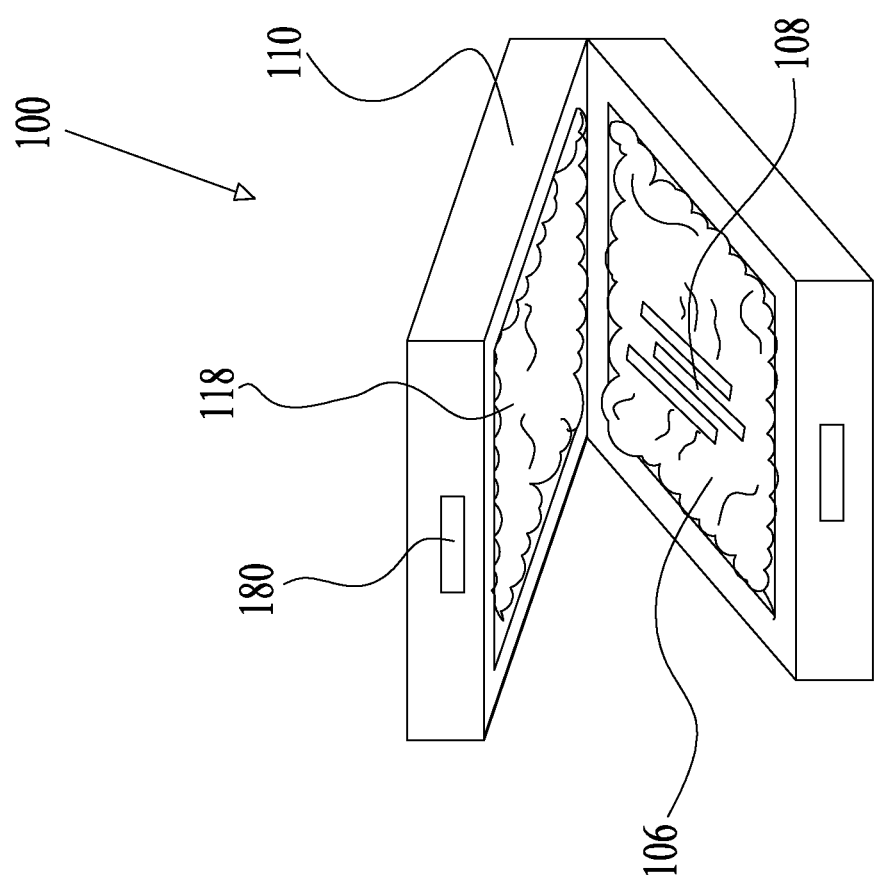

FIGS. 1A and 1B each illustrate an exemplary environmental condition control assembly 100 for controlling at least one environmental condition of a substance 102.

The substance may comprise in a non-limiting example, a drug, a biological or chemical substance, such as hormones, a growth hormone, blood, enzymes, body fluids, body parts, body organs, body tissue, sperms, or eggs. The substance may comprise analyte indicators, analyte sensors and/or analyte detectors comprising any type of material. The analyte indicator or sensor may comprise, for example, a blood glucose test strip configured for indicating the blood glucose level or any other analyte monitoring strip configured to detect the presence of analyte. The blood glucose strip or analyte strip may comprise enzymes or any other biological or chemical materials. In another example, the analyte indicator or sensor may comprise urine test strips. The analyte indicator or sensor may comprise any diagnostic tool based on a biological indicator comprising a biological and/or chemical material. The substance may comprise cosmetics, such as lipsticks, perfumes, toiletries, hair or skin care products, sprays, mousses, emulsions and gels, for example. The substance may comprise, resins, adhesives, glues, epoxy or cyanoacrylate glue. The substance may be configured in any suitable form, such as a solid, liquid, emulsion, gas, gel, granules, or powder, for example. The substance may include more than one substance at the same or different phase, such as, for example, a liquid mixed with another liquid or a liquid mixed with a powder. Wherein the substance comprises a drug, the drug may include any suitable form such as a solid, powder, tablet, pill, capsule, gas, gel, cream, emulsion, spray, a suppository or a combination thereof and may be delivered in any suitable manner.

In some embodiments, the substance may be contained within a container 104.

In some embodiments, the container 104 may comprise a substance storage device or a substance delivery device. The container 104 may be configured in any suitable configuration for containing a substance therein. In some examples the container 104 may comprise a device for drug injection delivery such as an injection pen, a jet injector and/or a syringe. Some further non-limiting exemplary containers 104 for containing substances may include a substance vial, a substance cartridge, an ampoule, a substance pump, a pill box, a capsule container, an inhalator, a substance spraying device, an infusion device with a pump or an infusion device without a pump. In some embodiments, the container 104 may comprise a box. In some embodiments, the container 104 may comprise a container for storing and transferring blood glucose strips or any other analyte, e.g. a biologic or chemical analyte monitoring strips.

In some embodiments, the container 104 may comprise or may be comprised in an environmental control sleeve as described in applicant's patent publication WO2016/011207 or an environmental condition control apparatus as described in applicant's patent publication WO2017/090019, both publications incorporated herein in their entireties.

In some embodiments, the substance 102 may be contained within the container 104 and the container 104 may be arranged within a receiving volume 106 (also referred to as a "chamber") of the environmental control assembly 100, as shown in FIGS. 1A and 1B.

As seen in FIG. C, in some embodiments, the substance 102 may be configured to be placed uncontained without a container 104, directly within the environmental control assembly 100. In a non-limiting example, the substance 102 may comprise analyte detector strips 108 placed directly within the environmental control assembly 100.

The environmental control assembly 100 may be deployed as a carrying or transporting case. A housing 110 may be provided to encase or otherwise contain or be part of a thermal insulator closure 114 (i.e. a first enclosure) comprising a thermal insulator material configured to provide a thermal shield to the substance 102, which may be contained within the container 104 or may be uncontained. The thermal insulator (may be interchangeably referred to as "insulation" or "isolation") closure 114 may be formed as a layer or any other structure of the thermal insulator material at least partially arranged intermediate or be part of the housing 110 and a deformable enclosure 118 (i.e. a second disclosure).

In some embodiments, the thermal insulator closure 114 is configured to provide a thermal shield to a volume at least partially contained in the housing.

In some embodiments, the thermal insulator material may comprise an evacuated chamber, such as a vacuum formed intermediate two walls 112 formed by the thermal insulator closure 114. In some embodiments, the thermal insulator closure 114 may comprise a vacuum insulated panel (VIP) comprising a gas-tight enclosure surrounding a rigid core, from which the air has been evacuated. In some embodiments, the thermal insulator closure 114 may comprise a multi-layered material formed of walls and evacuated gap, which may be commercially available as INSULON®, made by Concept Group, Inc. (www.conceptgroupinc.com), as well as similar constructions disclosed in U.S. Publication No. 20140090737, incorporated herein by reference in its entirety. In some embodiments, the thermal insulator closure 114 may comprise a relatively high-vacuum structure. In a non-limiting example the high-vacuum may be about $10^{-3}$ torr or less, or about $10^{-4}$ torr or less, or may be about $10^{-5}$ torr or less, or may be about $10^{-6}$ torr or less, or may be about $10^{-7}$ torr or less.

In some embodiments, the thermal insulator material may comprise silicon aerogel, air or any other gas or other materials, such for a non-limiting example, fiberglass, wool, cellulose, foams and/or polystyrene.

In some embodiments, as will be described in reference to FIGS. 5A-6, the thermal insulator closure 115 may comprise air enclosed between two surfaces or walls which can be rigid or flexible to further allow inflation or deflation of air or other gas between the surfaces or walls.

In some embodiments, several thermal insulation layers and/or materials having the same or different insulating properties may be used to achieve specific characteristics (e.g. degree of thermal insulation, predetermined temperature in the substance 102 for controlling and/or maintaining the environmental conditions of the substance 102).

The deformable enclosure 118 may reside within the insulator closure 114 and comprise at least one environmental control material 120 configured to regulate the environmental condition of the substance 102 and/or container 104. In some embodiments, the environmental control material 120 is contained within a deformable material or deformable surface. In a non-limiting example, wherein the environmental condition is temperature, the environmental control material 120 may comprise a PCM which is in at least partial thermal communication with the substance 102 and/or container 104. In some embodiments the deformable enclosure 118 may comprise a deformable surface.

Air is a poor thermal conductor. As such, formation of air pockets between the environmental control material 120 and the substance 102 and/or container 104 may decrease the effectiveness of the environmental control material 120 in controlling the environmental conditions. For example, wherein the environmental condition comprises temperature, air pockets or air gaps around the substance 102 and/or container 104 cause generation of non-uniform temperature areas around the container 104 (or around the uncontained substance 102), namely uneven distribution of heat around the container 104. This nonuniformity decreases the thermal conduction, causing the substance 102 and/or the container 104 to be inadvertently heated or cooled to a temperature out of a predetermined, desired range.

The deformable enclosure 118 may be formed at least partially of a deformable material/surface 124 (see insert in FIG. 2B) configured for enclosing the substance 102 and/or container 104 with at least partial physical and/or thermal contact therewith. Namely, the deformable enclosure 118 at least partially contiguously thermally and/or physically (namely mechanically) contacts the substance 102 and/or container 104 so as to minimize air-pockets or gaps formed intermediate the deformable enclosure 118 and the substance 102 and/or container 104. Accordingly, thermal conductivity between the substance 102 and/or container 104 and the environmental control material 120 is increased and the environmental control of the substance 102 and/or container 104 is maintained.

In a non-limiting example, wherein the environmental control condition is temperature, the increased thermal conductivity between the substance 102 and/or container 104 and the deformable enclosure 118 allows for maintaining temperature of the substance 102 and/or container 104 within a predetermined temperature range within any environment. Such an environment may include a refrigerator (domestic and/or industrial or any refrigeration) while being stored therein, and the environment further includes outdoors or out of refrigeration, such as during transportation or during use of the substance 102.

The deformable material 124 (which may comprise the deformable surface) may be formed of a thin layer. In a non-limiting example the width of the deformable material 124 may be within the range of about 0.1%-1% of the thickness of the environmental control material 120. In a non-limiting example the width of the deformable material 124 may be within the range of about 0.1%-10% of the thickness of the environmental control material thickness. In a non-limiting example the width of the deformable material 124 may be within the range of about 1-100 microns.

The deformable material 124 may comprise a flexible fabric or any other type of flexible material that provides sufficient thermal conductivity between the substance 102 and/or container 104 and the environmental control material 120.

In some embodiments, the environmental control material 120 may be formed of a plurality of environmental control material portions, such as with a first environmental control material portion 130 and second environmental control material portion 132. In a non-limiting example, the first portion 130 is configured with a relatively high phase transition temperature, such as, but not limited to, a phase change temperature in the range of about 4-30° C., or in the range of about 20-30 C°, or in the range of about 4-8° C., or in the range of about 8-20° C. and subranges thereof. The second portion 132 is configured with a relatively low phase transition temperature, such as, but not limited to, a phase change temperature in the range of 0-8 C°, or e.g. 2-8 C° or 0-2° C., and subranges thereof.

In other words, in some embodiments, there is an upper temperature limit "Tu" which should not be exceeded in order to prevent degradation (e.g. overheating) of the substance 102. The first portion 130 is thus selected with a first phase transition temperature less or equal to Tu. For example, the first portion 130 is configured to maintain an efficacious temperature of the substance 102 when in a warm ambient environment or when being stored in refrigeration and the refrigerator fails. There may be also a lower temperature limit "Tl" which dropping below it causes degradation (e.g. overcooling or freezing) of the substance 102. The second portion 132 is thus selected with a second phase transition temperature more or equal to Tl. For example, the second portion 132 is configured to maintain an efficacious temperature of the substance 102 and to prevents its overcooling or freezing, when in a cold or even freezing ambient environment or when the substance 102 is stored in the refrigerator (or freezer) or when being stored in refrigeration and the refrigerator fails.

Therefore, this combination of at least two environmental control material portions can control and protect the substance from both high as well as low ambient temperatures. Though two environmental control material portions are described, more than two different environmental control materials can be used. In some embodiments, the environmental control materials are preselected so that either one of them does not interfere with the functionality of the other even if they are all placed together, or if they might interfere, they are arranges in separate "chambers" or "pockets" or "enclosures" of the deformable enclosure 118 and in thermal contact with the substances 102 and/or containers 104.

In some embodiments, the environmental control material 120 comprises one or more thermal energy absorbing materials.

In some embodiments, the environmental control material 120 may comprise a phase change material (PCM) 126. The PCM 126 may include a material with relatively high heat of fusion which, by melting and solidifying (namely changing its phase) at a specific phase transition temperature, is capable of absorbing, storing and releasing relatively large amounts of energy. The PCM 126 further absorbs heat flux which may pass through the thermal insulator closure 114 before it reaches the substance 102 and/or container 104. The PCM 126 is configured to effect control and regulation of the environmental condition of the substance 102 and/or container 104. The PCM 126 may be characterized by its latent heat capacity and/or sensible heat capacity.

The PCM type may be characterized by its phase transition temperature, namely the temperature wherein the first phase fully changes to the second phase, such as the temperature at which the solids completely change into liquid. In some embodiments, the PCM type may be selected, inter alia, in accordance with any one of the following parameters: the required substance temperature, the time period required for maintaining the substance at the required substance temperature (or lower or higher than a predetermined temperature threshold) and the required mode (i.e. storage, typically refrigeration or use out of the refrigerator or transportation mode of the substance).

In some embodiments, the PCM 126 may comprise an organic based PCM, an inorganic based PCM, a eutectic based PCM, or a water based PCM. Non-limiting examples of inorganic PCM comprise salt hydrates, salts, metals and alloys. Non-limiting examples of organic PCM comprise paraffin, fatty acids, oils, biocompatible oils, vegetable oils, alcohols and glycols and an oleaginous substance.

The PCM 126 may be configured in any suitable form, such as in bulkform or microencapsulated form, for example. Microencapsulated PCMs may comprise capsules, generally with small diameters (in a non-limiting example a diameter of 1 micron to 1 centimeter). The PCM 126 is contained within the capsule. Microencapsulation allows mixing of different PCMs with different phase transition temperatures. When the PCM is in bulk form, each type of PCM may be maintained separately by enclosing each PCM in an individual compartment, or they can be housed in the same compartment if they do not interact with each other to modify the phase temperature or latent heat capacity (latent or sensible) of either one of them.

In some embodiments, in order to maintain the above-mentioned first portion 130 with the first phase transition temperature and the second portion 132 with a second phase transition temperature, the first portion 130 and the second portion 132 may be maintained unmixed. For example, by using microcapsules for each type of the first portion 130 and second portion 132, or by using microcapsules containing the first portion 130 dispersed within a bulk material of the second portion 132 (FIG. 1B). Furthermore the first portion 130 and the second portion 132 may be formed of a bulk of mutually immiscible materials such as a water based PCM for the first portion 130 and an oil based PCM for the second portion 132 or vice versa, thereby forming unmixed layers (FIG. 3B) that can be housed in the same compartment. The environmental control material 120 may comprise any other suitable combination of materials.

In some embodiments, the environmental control material 120 may comprise any suitable liquid. For a non-limiting example the liquid may comprise water, namely an $H_2O$ containing compound at it various phases (gas, liquid, solid). In some embodiments, a first environmental control material portion 130 may comprise the liquid and a second environmental control material portion 132 may comprise a PCM 126 as will be described in reference to FIGS. 1A and 1B.

In some embodiments, the liquid (e.g. water) contained within the deformable material 120 is provided to force the deformable enclosure 118 to assume and conform to the shape of the substance 102 or container 104, thereby increasing the thermal and/or physical contact between the deformable enclosure 118 and the substance 102 and/or container 104.

In a non-limiting example when the assembly 100 is designated to be refrigerated or in refrigeration temperature range (e.g. 2-8 C°), the first portion 130 may comprise a PCM configured to be in its solid phase (namely with a phase transition temperature below or equal to 8 C°) and with the second portion 132 comprising a PCM with a phase change temperature around 0-2 C°, or water. Thus when the assembly 100 is in ambient temperature above 8° C., the combination of PCM and insulation keeps the temperature refrigerated. While the second portion 132 PCM prevents the temperature of the substance from freezing, even if ambient temperature falls below freezing. This combination of the respective first and second portions 130 and 132 provides for maintaining the substance temperature within a temperature range below or equal to 8° C., but above freezing (e.g. 0° C. or less) even when the refrigerator temperature is not well controlled.

In some embodiments, the PCM may be configured to remain at least partially flexible also when it is in its solid form (below its phase transition temperature) temperatures. In a non-limiting example, such a flexible PCM in a compartment may be commercially available by Glacier Tekat https//glaciertek.com. These compartments contain PURE-TEMP® phase change materials commercially available from PURETEMP 4232 Park Glen Road, Minneapolis, MN 55416, USA.

In some embodiments, the environmental control material 120 may comprise a mixture of a PCM 126 and water 140. The mixture may be formed in any suitable manner such as a dispersed, wet-cake type mixture or as a dispersion of microcapsules comprising PCM 126 and water 140.

Any predetermined suitable ratio may be determined between the first environmental control material portion 130 and the second environmental control material portion 132. In a non-limiting example, wherein the first environmental control material portion 130 comprises a PCM 126 in any form and the second environmental control material comprises water 140, the first to second environmental control material ratio may be about 10:90 percent, or about 20:80 percent, or about 30:70 percent, or about 40:60 percent, or about 50:50 percent, or about 60:40 percent, or about 70:30 percent, or about 80:20 percent, or about 90:10 percent.

In some embodiments, the ratio is determined according to the environment surrounding the environmental control assembly 100. In a non-limiting example, the ratio may be selected according to the temperature stability of the domestic refrigerator storing the environmental control assembly 100. For a refrigerator with good temperature stability, which has a low risk of freezing the substances 102, the ratio may be such that most of the volume of the environmental control material comprises a PCM 126 and less water.

The environmental control material and the environmental control material portions may be provided in compartments. The compartments may be made of a flexible, deformable material 124 and contain the environmental control material 120 therein.

As seen in FIGS. 1A-1C, the environmental control material 120 comprises a mixture of water 140 and microencapsulated PCMs 126 provided in a first lower compartment 150 and a second upper compartment 152, thereby forming the deformable enclosure 118 for enclosing the container 104.

Figure 2B:
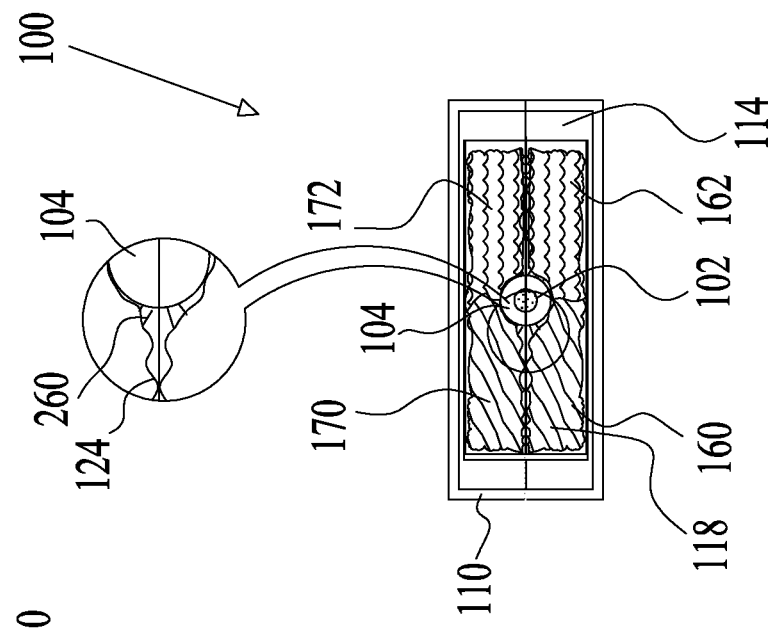
FIGS. 2A and 2B are a schematic illustration of an exemplary environmental condition control assembly at an open state (2A) and a sectional view at a closed state (2B) constructed and operative according to some embodiments of the present disclosure.
Figure 2A:
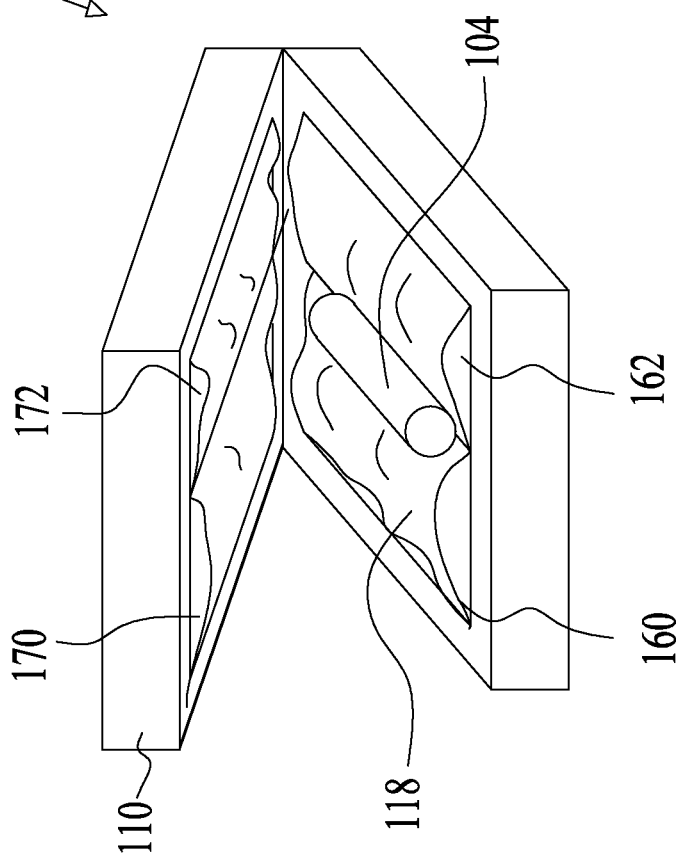

As seen in FIGS. 2A and 2B, a first and second lower compartment 160 and 162, respectively, may be provided and arranged alongside each other. A first and second upper compartment 170 and 172, respectively, may be provided and arranged alongside each other to form together the deformable enclosure 118 for enclosing the container 104. Each of the first and second lower compartments 160 and 162, and first and second upper compartments 170 and 172 may comprise the same or different environmental control material 120. As seen in a non-limiting example in FIGS. 2A and 2B, the first lower compartment 160 and the first upper compartment 170 comprise a first PCM 126 bulk, while the second lower compartment 162 and the second upper compartment 172 comprise water.

Turning to FIGS. 3A and 3B it is shown that the first and second lower compartments 160 and 162, respectively, may be provided and arranged to overlay each other. First and second upper compartments 170 and 172, respectively may be provided and arranged to overlay each other thereby forming together the deformable enclosure 118 for enclosing the container 104. Each of the first and second lower compartments 160 and 162, and first and second upper compartments 170 and 172 may comprise the same or different environmental control material 120. As seen in a non-limiting example in FIGS. 3A and 3B, the first lower compartment 160 and the second upper compartment 172 comprise a PCM 126 while the second lower compartment 162 and the first upper compartment 170 comprise water.

It is appreciated that FIGS. 1A-3B are examples of environment control materials and arrangements thereof and any combination or arrangement of environment control materials may be used.

The thermal insulator closure 114 and the deformable enclosure 118 may be manufactured in any suitable process, such as by being synchronously injected or by being separately manufactured and joint together thereafter. In some embodiments, the deformable enclosure 118 may be configured such that whereupon there is a plurality of environmental control material portions, the container 104 or substance 102 is substantially in equal contact with each of the portions.

In some embodiments, the deformable enclosure 118 comprises an environmental control material 120 formed of a deformable material and the deformable material is obviated.

In some embodiments, the environmental control assembly 100 may comprise a locking mechanism 180 (FIG. 1A) formed in any suitable manner for closing an upper part 182 against a lower part 184 of the environmental control assembly 100 in a tight sealed engagement. Thus establishing thermal and physical contact between the deformable enclosure 118 and the substance 102 and/or container 104. The locking mechanism 180 may comprise any suitable form of mechanical locks, in a non-limiting example plastic resealable zippers (e.g. ZIPLOC® or zipper locks.

In some embodiments, the environmental control assembly 100 may comprise a thermally self-recharging assembly 100. This may be achieved by selecting an environmental control material 120 comprising passive elements, such as a PCM 126 and/or water 140, without requiring any electrical power to operate the environmental control material 120. The environmental control material 120 may be selected according to ambient temperature fluctuations, appropriate volume and according to the substance temperature maximal or minimal limit. For example, by selecting any one or more PCMs with a phase transition temperature equal or slightly below a maximal substance temperature limit and selecting a PCM volume configured to remain at a solid phase for a predetermined time period, due to the combination of insulation and PCM, the substance may be safely maintained below the maximal substance temperature limit for a relatively long period, including during use and/or storage of the container 104 within the assembly 100 even when exposed to temperature conditions outside (greater or lower than) the safe temperature of the substance, and regain that capacity without any special, unordinary user intervention.

The ambient temperature may include a temperature out of the assembly 100, such as a refrigeration temperature, when the assembly 100 is stored in the refrigerator, and the outdoor temperature, when the assembly 100 is placed out of the refrigerator.

In a non-limiting example, for such a thermally self-recharging assembly 100, substance 102 comprising insulin may retain its efficacy until expiry date set by the manufacturer if maintained in a temperature below 8° C. By selecting a PCM 126 with a phase change temperature close to the temperature limit of 8° C., such as 7° C. or 8° C., with the PCM sufficient volume, the receiving volume 106 will not exceed the 8° C. limit as long as the PCM 126 does not completely change its phase from solid to liquid. Thus even if the assembly 100 is placed in an ambient temperature of over 8° C. (e.g. room temperature) for slightly less than 12 or less than 24 hours, the insulin will remain below 8° C. Whereupon the ambient environment returns to temperature below the phase transition of the PCM (e.g. below 7° C. or 8° C.)., such as when the refrigerator is active again or the assembly 100 is returned to a refrigerator that works properly, the PCM 126 will start to solidify again, without requiring the user to invest electrical energy. Since it is normal for users to place unused insulin in refrigeration, the assembly 100 allows the user to bring refrigerated insulin from the pharmacy back home and place it in the refrigerator without special, unordinary user action, the user is required to remove the assembly 100 from the refrigerator, reach the pharmacy, place the refrigerated insulin inside the assembly 100 and return home and place the insulin in the refrigerator, as usually performed by a user.

Figure 9:
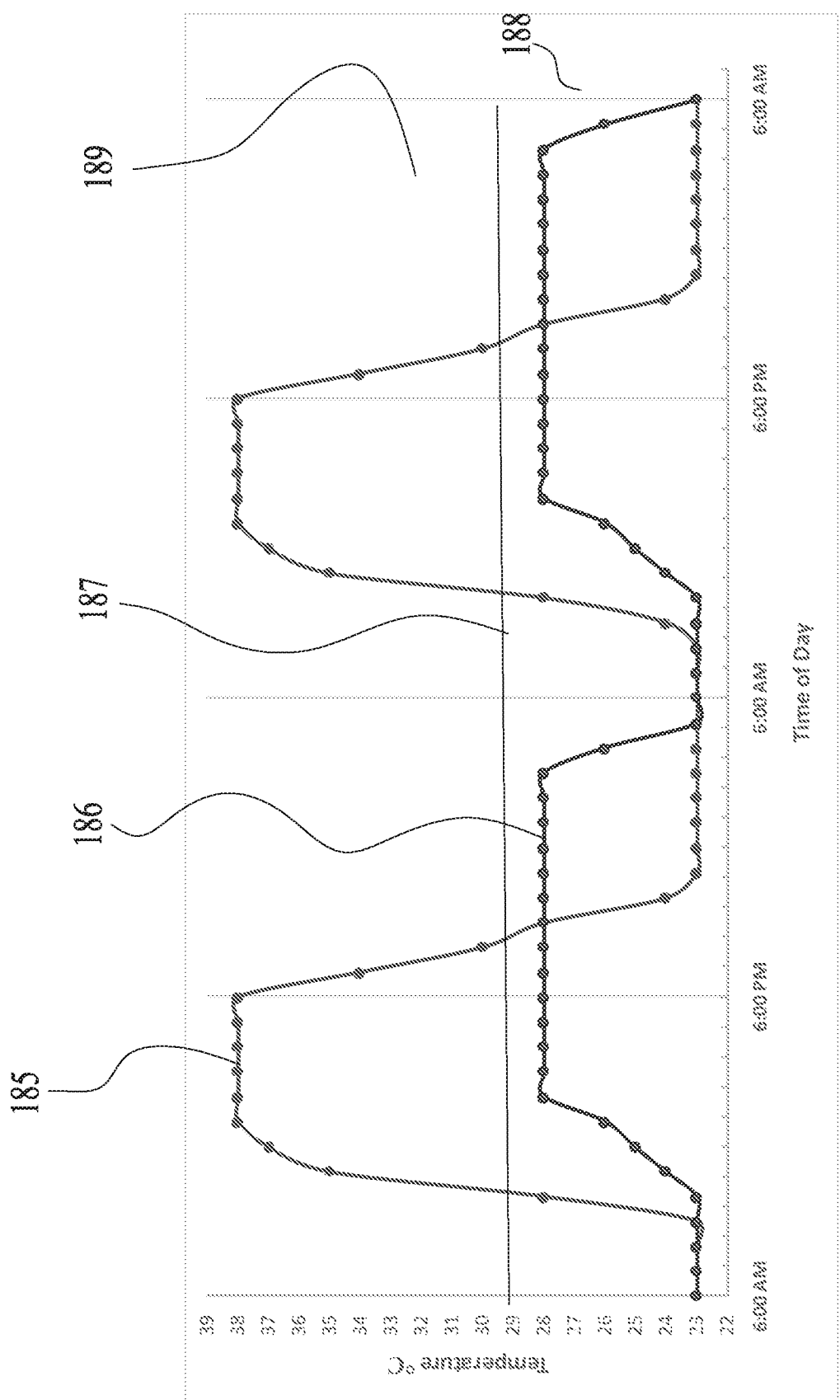
FIG. 9 is a graph of an exemplary performance of the environmental condition control assembly constructed and operative according to some embodiments of the present disclosure.

Operation of an exemplary assembly 100 is shown in the graph of FIG. 9. A two day cycle is shown. The upper graph 185 shows the ambient environment temperature changes as it cools at night and heats during daytime. The lower graph 186 shows the temperature changes inside a container 104 comprising a insulin pen injector and encased in an assembly 100, as it rises and lowers in its self-recharging assembly 100 continuously and cyclically. The substance temperature is maintained, without unordinary intervention, below the upper threshold line 187, thereby ensuring the substance 102 in well in its safe temperature zone 188 and away from the unsafe temperature zone 189.

The assembly 100 performing as a self-recharging assembly is greatly advantageous. As described, the temperature of the substance 102 is maintained within is officious temperature range. This is without danger of freezing since the assembly is configured to self-recharge without the need to insert in a freezer (as required when using conventional ice packs) or cumbrously changing cases when transporting from the pharmacy to the refrigerator. The user may use the assembly 100 for containing the substance 102 in a continuous manner without requiring special, unordinary intervention on his part, as the recharging of the assembly 100 is performed without user intervention.

Figure 4:
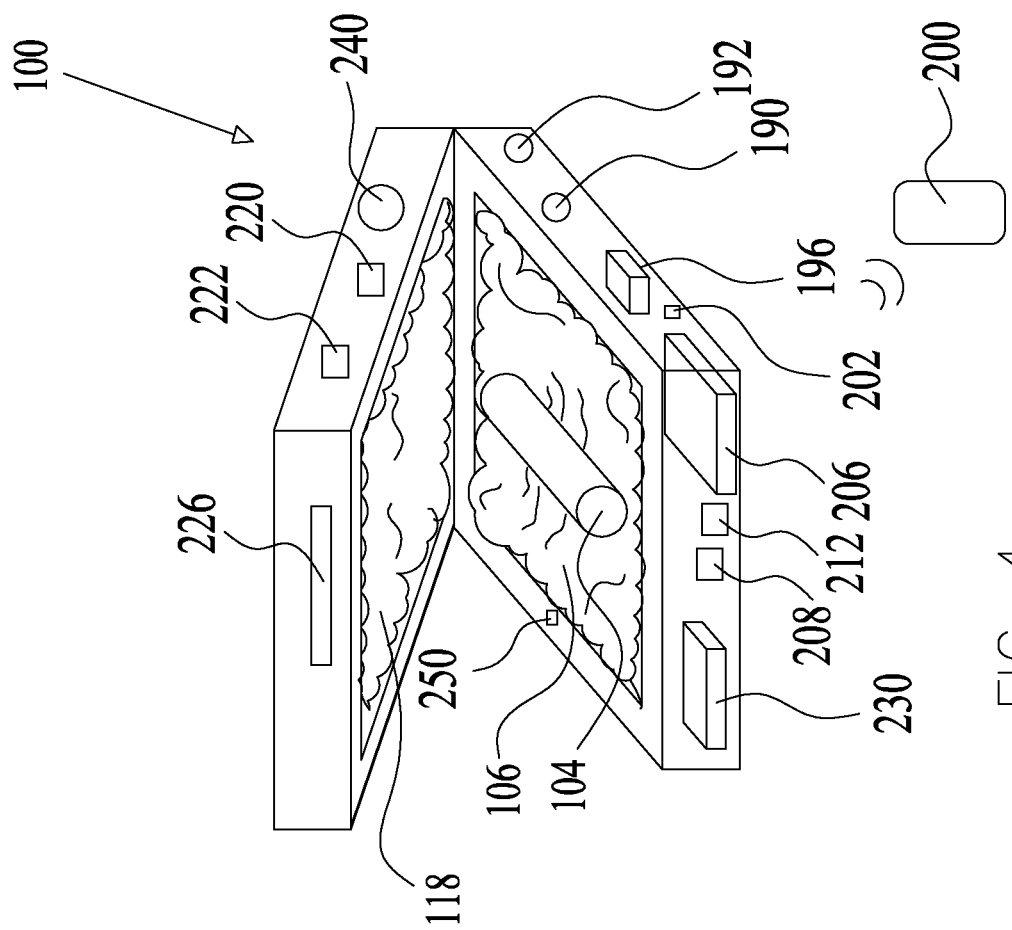
FIG. 4 is a schematic illustration of an exemplary environmental condition control assembly constructed and operative according to some embodiments of the present disclosure.

As seen in FIG. 4, the assembly 100 may comprise any one of the following components: at least one or more temperature sensors 190 designed to monitor the temperature of the receiving chamber 106 and/or the container 104 and/or the substance 102 and/or the ambient environment out of the assembly 100. In some embodiments, a component may comprise presence sensors 192, designed to monitor the presence of container 104 and/or substance 102 within the receiving chamber 106 or removal therefrom. In a non-limiting example, the presence sensors 192 may comprise an RFID tag reader or a camera, a switch or other detector, such as an optical or electronic detector for example. Exemplary additional sensors may include capacitive sensors and accelerometer sensors which may be employed to detect touch of the assembly 100 or removal of the container 104 from the assembly 100 thereby detecting presence of the container 104.

In some embodiments, an external device 200 may be provided to receive signals or data from the assembly 100 (e.g. from sensors 190 or 192) via a wireless transponder or any other suitable communication means 202, such as a wired USB connector port or any other wired or wireless connector port. The external device 200 may comprise a remote device e.g. a Smartphone, a computer or any device with a processor.

The assembly 100 may comprise components, such as a power source, e.g. a battery 206 positioned at any suitable location. The assembly 100 may comprise electronics 208, such as a thermistor, a transistor, boards, wires or circuitry and/or a control circuit for controlling electrical components of the assembly 100. Electrical connections (not shown) between the battery 206, and the controller 196, electronics 208 and any other electrical component, may be provided.

In some embodiments, the assembly 100 may comprise components, such as a memory device, and/or a timer, for example.

In some embodiments, the battery 206 may be disposable. Since the passive control elements (e.g. the deformable enclosure 118, the insulation closure 114) do not require much power, the battery 206 may be operative for a relatively long time, such as for days, months or years. In some embodiments, the battery 206 may be rechargeable. Recharging may be performed via a recharging port 212 or via inductance, solar recharging means or other means which allow electrical charge generation.

In some embodiments, the assembly 100 may comprise one or more indicators 220, such as LED indicators or a small electronic display, for example. The indicators 220 may indicate one or more environmental conditions of the substance 102, such as the drug temperature, or any other parameter of the drug, such as color, clarity or transparency, for example. The indicators 220 may be configured in any suitable manner such as described in applicant's patent publication WO2017/090019, incorporated herein in its entirety.

According to some embodiments, there may be provided a control capacity indicator 222 configured to display the remaining control capacity provided by the environmental control material 120 to maintain the required environmental conditions. For example, a PCM 126 is capable of absorbing the heat flux from the ambient environment until the volume of the PCM 126 fully liquidizes from a solid phase to a liquid phase. The PCM volume yet to undergo a phase change from solid to liquid is indicative of the remaining thermal control capacity of the environmental control material 120. The control capacity indicator 222 may be configured as described in applicant's patent publication WO2017/090019, incorporated herein in its entirety.

The assembly 100 may comprise further components, such as an electrically powered thermoelectric element 230 or any other heating element, heater or cooler or fan for further controlling the environmental condition (e.g. temperature) of the (inside the) assembly 100. In some embodiments, the controller 196 may be configured to control the operation of the thermoelectric element or heater or cooler 230 according to the temperature detected by the temperature sensor 190. In some embodiments, more than one temperature sensor is used. In some embodiments there may be at least one temperature sensor for monitoring the ambient temperature and at least one temperature sensor for monitoring the temperature inside the assembly (i.e. that of the substances 102). In some embodiments, the thermoelectric element 230 or any other heating element or heater is configured to heat the substance 102 while not exceeding a maximal temperature efficacy limit of the substance.

Furthermore, to conserve energy of the power source 206, some of the components may be configured to be inoperative at certain times. Upon detection of a predetermined event, such as insertion of the container 104 into the assembly 100 or any other event, components may be activated for a predetermined time period and shut off thereafter. In some embodiments, an accelerometer, a vibration, capacitive or movement sensor and/or the presence sensor 192 may be used to detect the predetermined event.

In some embodiments, the assembly 100 may comprise a fan 240 to further enhance uniform distribution of heat within the deformable enclosure 118 and thus achieve a uniform temperature along or around the container 104 and/or substance 102. In some embodiments, the fan 240 is activated by the controller 196 wherein it is measured by the temperature sensors 190 that the temperature in not uniform along the container 104 and/or substance.

In some embodiments, a camera or other optical detector or detectors array or matrix 250 may be provided at any suitable location within the deformable enclosure 118 to image (or provide optical information relating to) the substance 102 and/or container 104 and/or the deformable enclosure 118. The camera 250 may transmit the images or other optical information (at visible or invisible optical wavelengths), which may be still photos or streaming images, or optical information, such as a video, either wired or wirelessly to the external device 200.

In some embodiments, the assembly 100 may comprise further elements for enhancing the thermal conductivity between the PCM contained at least partly by the deformable enclosure 118 and the substance 102 and/or container 104. For example, one or more thermal conducting layers 226 or any other structure formed of a thermal conductor, e.g. a metal, such as copper, generally in a relatively flexible state, may be arranged within the deformable enclosure 118.

In some embodiments, flexible fins 260 (insert of FIG. 2B) or any thermal conduction element may be provided within the deformable enclosure 118. The fins 260 are flexible to fit and conform to the shape of the substance 102 and/or container 104 and provide for uniform thermal conduction from the deformable enclosure to the substance 102 and/or container 104. Accordingly, the thermal conduction is improved even when the PCM 126 is in its solid phase and some slight air gaps may appear such that the conformity of the PCM 126 to the shape of the substance 102 and/or container 104 may be compromised. The flexible fins 260 may be formed of a material with relatively high thermal conductivity, such as in a non-limiting example, a plastic covered with aluminum or just aluminum foils secured to the inside of the deformable enclosure 118.

The housing 110 may be formed in any suitable manner. In some embodiments, the housing may be formed of a rigid material, such as a hard plastic, as seen in FIGS. 1A-4. In some embodiments, the housing may be formed of a flexible, deformable material. In a non-limiting example the housing 110 may be formed of any shape, such as cylindrical, round, oval, spherical, or box shape or any other suitable shape.

As seen in FIGS. 5A-6, the housing 110 may be formed of an inflatable subassembly 300. In some embodiments, the inflatable subassembly 300 also includes the thermal insulation enclosure 114. The inflatable subassembly 300 comprises two spaced apart walls 302 where at least one of them is formed of a deformable material. The walls 302 form an air gap 306 therebetween which may be inflated to generate the insulation of the thermal insulation enclosure 114. Upon inflation, the inflation walls 302 may press against the deformable enclosure 118 positioned therein, which is turn conforms to the shape of the one or more substances 102 and/or containers 104 and is in thermal and physical contact with the one or more substances 102 and/or containers 104.

The inflatable subassembly 300 may be inflated in any suitable manner. In some embodiments, there may be provided an air or any other gas inlet 310 formed with an aperture 312 for allowing air (or other gas) to flow therein. The air (or other gas) may be introduced in any suitable manner, such as via a manual or electrical pump 320, typically comprising a piston or any other means for pressing air (or other gas) into the inlet 310. The pump 320 may comprise a valve 330 or any other means for controlling the airflow therein. In some embodiments, another gas besides or in addition to air may be employed to inflate the inflatable subassembly 300. In some embodiments, the pump 320 may be provided with a compressed gas tank for use of the gas to inflate the inflatable subassembly 300. In some embodiments, the inlet 130 may protrude out of the housing 110, as shown in FIGS. 5A-6, in some embodiments the inlet 310 may be inserted in the housing 110, as seen in FIG. 6B.

The flow of the air/or gas in and/or out of the inflatable subassembly 300 may be controlled by the controller 196 (FIG. 4) and the valve 330, and may be configured to introduce or release air or gas or pressure from the inflatable subassembly 300 in accordance with the environmental conditions or in accordance with any other parameters.

In some embodiments, the air inlet 310 may be used as a mouthpiece for humanly inflating the inflatable subassembly 300.

The inflatable subassembly 300 may comprise the locking mechanism 180 of any suitable form located in at least one facet of the device. In some embodiments the locking mechanism 180 may extend along the rim 350 of the inflatable subassembly 300 to seal the rim 350. In some embodiments, the locking mechanism 180 may be configured to be opened to allow removal of a container 104 and/or substance 102 from the assembly 100. In a non-limiting example, the locking mechanism 180 may comprise a zipper.

As seen in FIG. 5A, one or more containers 104 may be placed within the receiving volume 106 of the assembly 100 while the inflatable subassembly 300 is in its initial pre-inflated (i.e. deflated) state. The inflatable subassembly 300 may be inflated in any suitable manner to its inflated state, as seen in FIGS. 5B and 5C. The inflated walls 302 and air gap 306 therebetween create the thermal insulation enclosure 114, which in turn presses upon the deformable enclosure 118, here shown in FIG. 5C comprising a first portion 130 with a first type of PCM and a second portion 132 with a second type of PCM and encased in two compartments. The pressed deformable enclosure 118 conforms to the shape of the plurality of containers 104 and thus minimizes air gaps and thermally and physically contacts the containers 104.

In some embodiments, the inflatable subassembly 300 may be deflated by removable of the air therefrom, typically via the air inlet 310. This deflatable state may be generated whereupon there is a need to rapidly change the temperature of the substance 102 or that of the receiving volume 106, which can be facilitated by deflation of the insulation formed by the inflated walls 302. For example, whereupon the assembly 100 is first stored in refrigeration it may be desired to rapidly lower the temperature of the receiving volume 106 to accelerate the time it takes for the PCM to turn solid and allow the introduction of refrigerated substances inside. Accordingly, the inflatable subassembly 300 may be deflated to remove the insulation and allow the temperature of the PCM 126 to equalize faster with the ambient temperature.

In some embodiments, the inflatable subassembly 300 may be configured to be non-deflatable and may optionally comprise a one-way valve or any other means to prevent the deflation of the inflatable subassembly 300.

In some embodiments, the inflatable subassembly 300 comprises an inflatable structure in addition to a separate thermal insulation enclosure 114.

In some embodiments, the inflatable subassembly 300 may be configured to encase substantially the entire substance 102 and/or container 104, as shown in FIGS. 5A-5C wherein the containers 104 are inserted into the assembly 100.

Figure 6A:
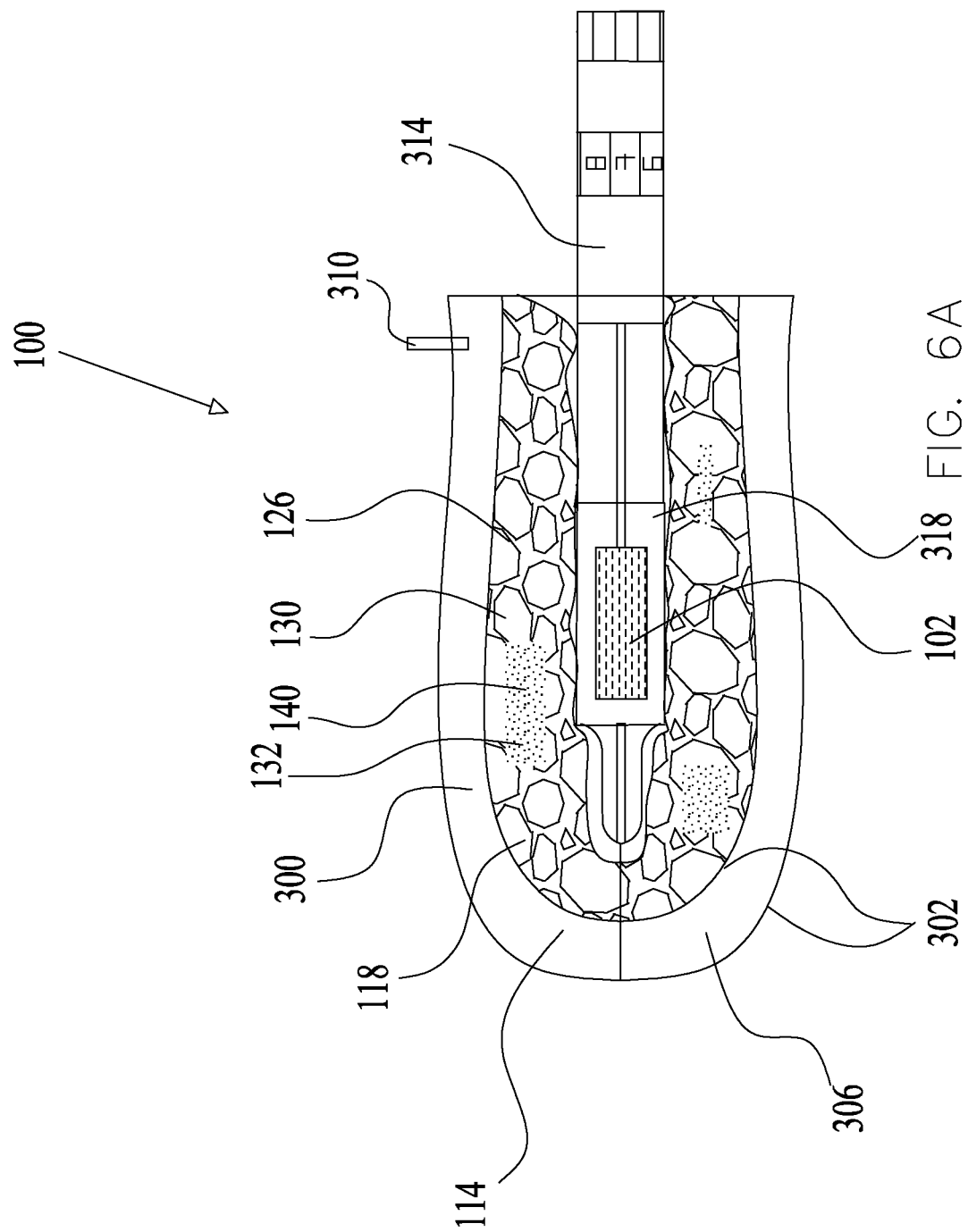
FIGS. 6A and 6B are each a schematic illustration of an exemplary environmental condition control assembly constructed and operative according to some embodiments of the present disclosure.
Figure 6B:
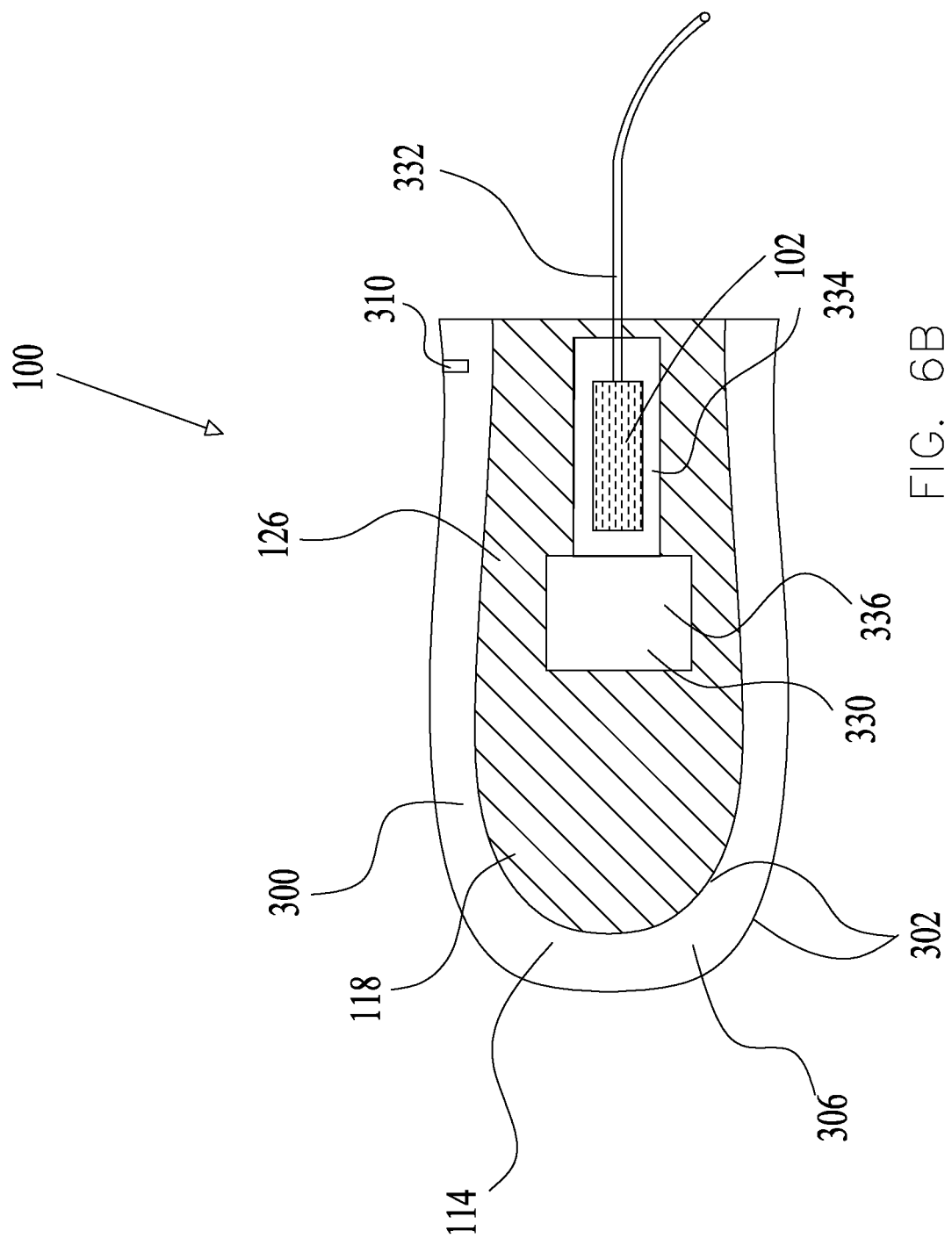

Turning to FIG. 6A it is seen that that in some embodiments the inflatable subassembly 300 may encase or envelope only a portion of the container 104 (or substance 102).

The container 104 here is shown comprising a drug injection device, such as a pen injection device 314 for delivering the substance 102 (i.e. the drug) positioned with a substance reservoir 318. The inflatable subassembly 300 is configured to encase only a portion of the container 104. Typically this portion comprises the substance reservoir 318. The inflatable subassembly 300 may be inflated via the air inlet 310. In its inflated state, shown in FIG. 6A, the inflated walls 302 and air gap 306 therebetween create the thermal insulation enclosure 114, which in turn presses upon the deformable enclosure 118, here shown including a first portion 130 comprising microencapsulated or bulk PCM 126 arranged or immersed in a second portion 132 comprising water 140 or other PCM 126. In some embodiments a single type of PCM 126 may be used. The pressed deformable enclosure 118 conforms to the shape of the encased portion of the container 104 and thus minimizes air gaps while thermally and physically contacting the encased container portion.

As seen in FIG. 6B, the container 104 may comprise a drug infusion device 330 which may comprise a catheter 332 in fluid communication with a drug reservoir 334 for delivering the substance 102 (i.e. the drug) positioned within the substance reservoir 334. The infusion of the drug from the reservoir 334 to the catheter 332 may be facilitated by a pump 336, which may be positioned proximal to the reservoir 332, as seen in FIG. 6B, or remote therefrom. The inflatable subassembly 300 is configured to encase only a portion of the container 104. Typically this portion comprises the substance reservoir 332. The inflatable subassembly 300 may be inflated via the air inlet 310. In its inflated state, shown in FIG. 6B, the inflated walls 302 and air gap 306 therebetween create the thermal insulation enclosure 114, which in turn presses upon the deformable enclosure 118, here shown including a single type of PCM 126. The pressed deformable enclosure 118 conforms to the shape of the encased portion of the container 104 and thus minimizes air gaps while thermally and physically contacting the encased container portion.

It is noted that the assembly 300 may comprise any one of the features described in reference to assembly 100, mutatis mutandis.

Figure 7:
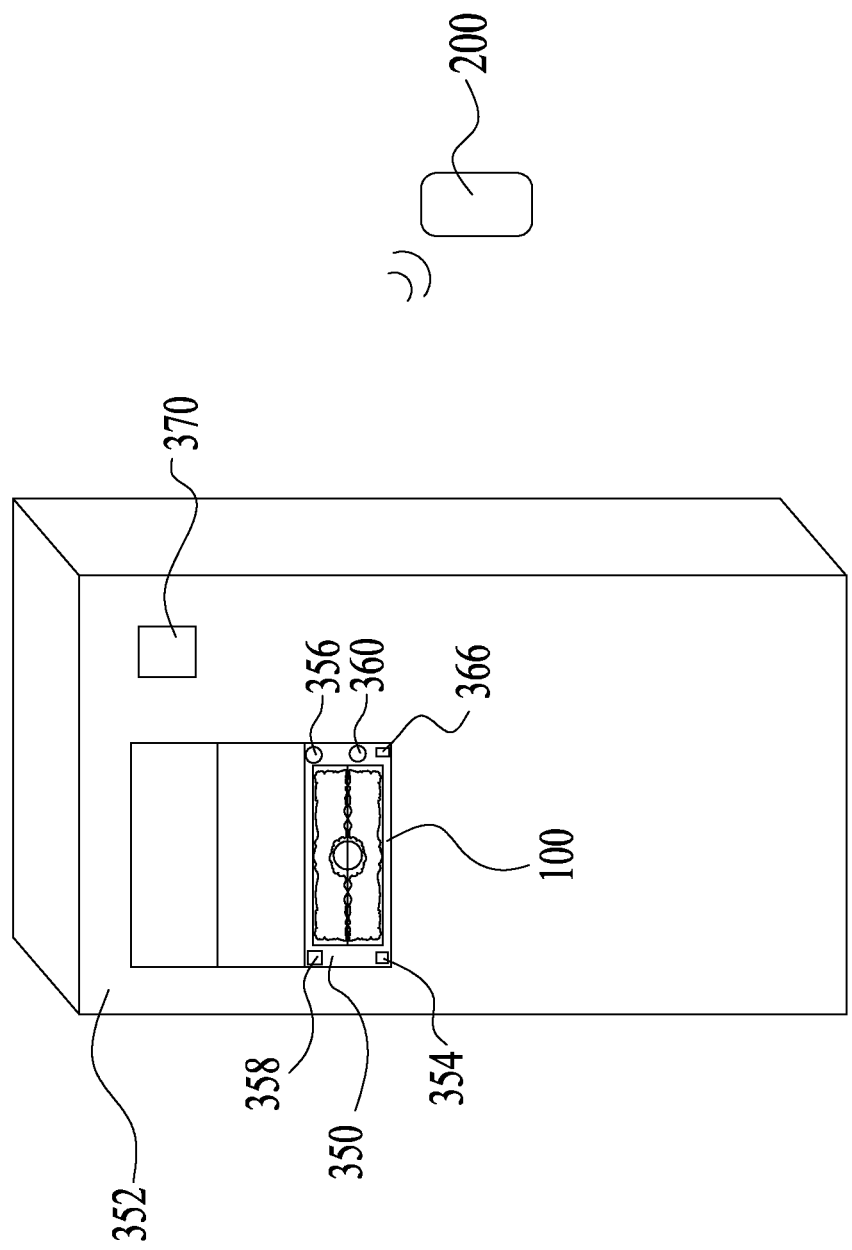
FIG. 7 is a schematic illustration of an exemplary environmental condition control assembly incorporated within a refrigerator, constructed and operative according to some embodiments of the present disclosure.

In some embodiments, there is provided an environmental control system for controlling the environmental condition of the substances, wherein in a portion of the system the environmental condition is uncontrolled, as shown for example in FIGS. 6A-7.

As seen in FIG. 7, in some embodiments, the assembly 100 may be configured to be placed inside a designated environmental control, refrigeration compartment 350 of a refrigerator 352, in a non-limiting example, a domestic refrigerator. The compartment 350 may be a designed built-in feature of a commercial refrigerator. The compartment 350 is sized and constructed to house the assembly 100 and to allow the assembly 100 to be removable therefrom.

In some embodiments, the compartment 350 may comprise components such as an electrically powered thermoelectric element or any other heater or cooler 354 for further controlling the environmental condition (e.g. temperature) of the assembly 100. In some embodiments, the refrigeration compartment 350 may comprise a temperature sensor 356 for measuring the temperature of the container 104 and/or substance 102.

In some embodiments, a controller 358 may be provided and may be configured to control the operation of the thermoelectric element or heater or cooler 354 according to the temperature detected by the temperature sensor 356. The thermoelectric element or heater or cooler 354 may be operated to prevent the substance 102 from exceeding an upper temperature limit or from being less than a lower temperature limit. In some embodiments, the refrigeration compartment 350 may comprise a presence detector 360 for detecting the presence of the assembly 100 and/or the container 104 in the refrigeration compartment 350 or removal therefrom. Communication means 366 may be provided to transmit signals received from the presence detector 360 and/or the temperature sensor 356 to the external device 200. The signals may be received by the external device 200 directly from the presence detector 360 and/or the temperature sensor 356 or via a control unit 370 (such as a standard pre-existing controller) of the refrigerator 352 or by any other suitable means.

In some embodiments, the substance 102 may contain food and the assembly 100 of any of the configurations shown herein in FIGS. 1A-8, may be configured to control the temperature of the food. For example, the food, in any solid and/or liquid or combined form, may be placed within the assembly 100 at a relatively high temperature (e.g. above 60° C.) and may be so maintained within the assembly 100 for a long time period, such as a few hours to a period of over 24 hours or more to days. The food may be maintained at a desired temperature in an untethered environment or off-grid environment and kept hot and unspoiled within the assembly 100, acting as a lunchbox. Similarly, for example, the food may be placed within the assembly at a relatively low temperature (e.g. below 10° C. and even lower than 0° C.) and may be so maintained within the assembly 100 for a long time period, such as a few hours to a period of over 24 hours or more to days while maintaining the food cold and fresh. The housing 110 may be formed of a rigid material (FIG. 1A-1C) or may be formed of a deformable material and/or may be formed of the inflatable subassembly 300 (FIGS. 5A-6).

It is appreciated that in some embodiments the assembly 100 may be configured to be used for a plurality of containers 104, even in a large scale. In a non-limiting example, the assembly 100 may be sized and configured for containing tens or even hundreds or more containers 104. In some embodiments, the assembly 100 may be configured as a drug cabinet or a drug transportation box for safely transporting a drug, even for long time periods (days, weeks or months). The drug cabinet or box may comprise ant one of the components (e.g. sensor temperatures) described herein.

In some embodiments the assembly 100 may be sized to be handheld and/or portable. In a non-limiting example, the assembly 100 may be sized to be positioned in a backpack or suitcase or any other typical means for a user carrying supplies. In a non-limiting example, the assembly 100 may be sized to fit a user's pocket, purse and/or handbag, for example. In some embodiments, the assembly 100 may be configured and sized to be transported by a drone. Since the substance 102 and/or container 104 is encased at least partially by the assembly 100, when transporting by drone or any other suitable transpiration mean there is no need for equipping the drone with a separate, auxiliary thermal storage element.

The assembly 100 is configured to provide uniform heat distribution, namely temperature along the substance 102 and/or container 104. In the embodiments of FIGS. 1A-7 this is achieved by providing the deformable enclosure 118 to conform to the shape of the substance 102 and/or container 104 and thereby minimizing air gaps. The deformable enclosure 118 may be configured as a heat distribution means.

Figure 8:
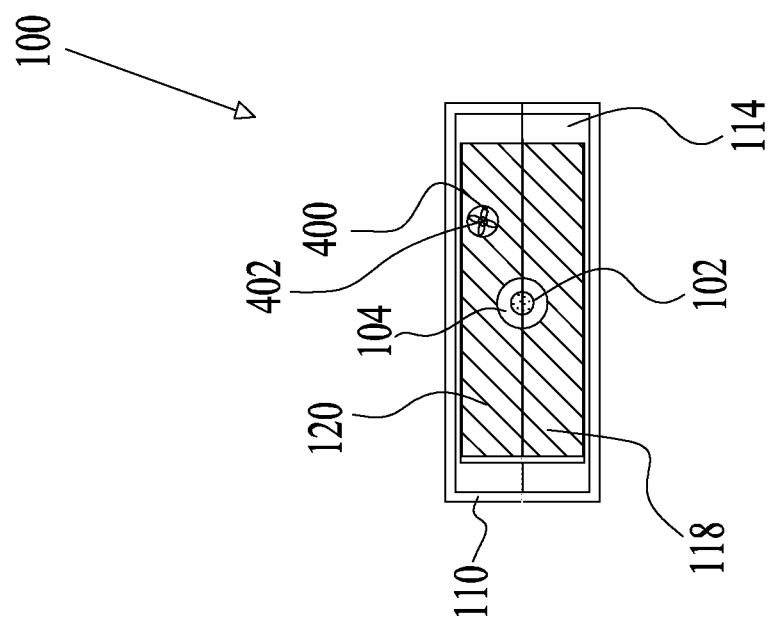
FIG. 8 is a schematic illustration of an exemplary environmental condition control assembly constructed and operative according to some embodiments of the present disclosure.

As seen in FIG. 8, uniform heat distribution may be provided in other suitable manners. For example, the assembly 100 may comprise the thermal insulation enclosure 114 and an environmental control material 120 in at least partial thermal communication with a substance 102 and/or container 104. The assembly 100 may comprise a uniform heat distributor 400 for distributing heat uniformly by any means of heat conduction, heat convection and/or radiation. In a non-limiting example, the distribution means 400 may comprise a fan 402 for blowing air, which was inadvertently trapped around the substance 102 and/or container 104, along the substance 102 and/or container 104 and thus preventing nonuniform heat distribution therealong.

While the disclosure has been described with respect to a limited number of embodiment, it is to be realized that any combination of embodiments in whole or part can also be used and that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B), in another embodiment, to B only (optionally including elements other than A), in yet another embodiment, to both A and B (optionally including other elements), etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B), in another embodiment, to at least one, optionally including more than one, B, with no A present (and optionally including elements other than A), in yet another embodiment, to at least one, optionally including more than one, A, and at least one, optionally including more than one, B (and optionally including other elements), etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An environmental control assembly for controlling at least one environmental condition of one or more substances, the one or more substances being uncontained or contained within a substance container, the assembly comprising:
   a first enclosure comprising a thermal insulator configured to provide a thermal shield to the substance,
   a second enclosure comprising:
      at least one environmental control material configured to regulate the at least one environmental condition of the substance, and comprising a deformable material including a phase change material contained in microcapsules and being configured to conform to the shape of the any one or more substance and substance container; and
      at least one deformable surface configured to conform to the shape of the any one or more substance and substance container and encase the one or more substance and substance container, the at least one deformable surface at least partially physically contacts with at least one or more of the substance and the substance container,
   wherein the first enclosure at least partially encases the second enclosure,
   and
   a housing at least partially comprising the first enclosure and the second enclosure, wherein the phase change material microcapsules are thermally self-recharging including thermally self-recharging in a non-freezing ambient environment.

2. The assembly according to claim 1, wherein the second enclosure forms a chamber configured to receive at least one of the substance and the substance container, and
   the second enclosure is configured to contiguously contact at least one of the substance and the substance container so as to minimize air-pockets formed intermediate the deformable surface and at least one of the substance and the substance container.

3. The assembly according to claim 1, wherein the second enclosure comprises at least one compartment and wherein at least two types of environmental control materials are mixed together and placed in the at least one compartment.

4. The assembly according to claim 1, wherein the second enclosure comprises a plurality of compartments and each compartment comprises a single type of environmental control material.

5. The assembly according to claim 4, wherein the plurality of compartments includes a first compartment and a second compartment, the first compartment comprises a first type of environmental control material and the second compartment comprises a second, different type of environmental control material.

6. The assembly according to claim 1, wherein the environmental control material comprises an additional type of phase change material (PCM).

7. The assembly according to claim 6, wherein the additional type of PCM includes a of bulk PCM.

8. The assembly according to claim 1, wherein the environmental control material comprises a first type of environmental control material and a second type of environmental control material, the first type of environmental control material comprises the PCM microcapsules and the second type of environmental control material comprises H2O.

9. The assembly according to claim 8, wherein the ratio of the PCM microcapsules to H2O is in the range of about 1:1 (one to one) to about 10:1 (ten to one) (PCM microcapsules to H2O).

10. The assembly according to claim 1, further comprising a heating element configured to heat the substance.

11. The assembly according to claim 10, wherein the heating element is configured to heat the substance while not exceeding a maximal temperature efficacy limit of the substance.

12. The assembly according to claim 1, further comprising a power source.

13. The assembly according to claim 1, further comprising a locking mechanism for closing the housing.

14. The assembly according to claim 1, further comprising communication means for wired or wirelessly communicating with a remote device.

15. The assembly according to claim 1, wherein the substance is selected from a group consisting of a drug, a biological substance, a hormone, a growth hormone, blood, enzymes, a body fluid, a body part, a body organ, a body tissue, a sperm, an egg, an analyte indicator, a blood glucose test strip, an enzyme, a urine test strip, a biological indicator comprising a biological and/or chemical material, a cosmetic, lipstick, a perfume, toiletries, sprays, mousses, emulsions, gels, resins, adhesives, glues, epoxy and cyanoacrylate glue.

16. The assembly according to claim 1, wherein the housing is formed of a rigid material.

17. The assembly according to claim 1, wherein the housing is formed of a flexible material.

18. The assembly according to claim 1, wherein the first enclosure comprises a selectively inflatable and/or deflatable closure configured to introduce air therein upon inflation thereof and remove the air therefrom upon deflation thereof.

19. The assembly according to claim 1, wherein the assembly is configured to be placed within a compartment of a refrigerator that is sized and constructed to house the assembly.

20. The assembly according to claim 19, wherein the assembly is configured to be removable from the refrigerator compartment.

21. An environmental control system for controlling at least one environmental condition of one or more substances, the one or more substances being uncontained or contained within a substance container, the system comprising: an environmental control assembly according to claim 1, and a portion wherein the environmental condition is uncontrolled.

22. The system according to claim 21, wherein the system comprises a refrigerator.

23. The system according to claim 21, wherein the system comprises a drug infusion device.

24. The system according to claim 1, further comprising a heat distributor configured for distributing heat along the one or more substance and substance container.

25. The assembly of claim 1, wherein the microcapsules are formed of a diameter in the range of 1 micron to 1 centimeter.

26. The assembly of claim 1, wherein the deformable environmental control material and the deformable surface are configured to conform to containers of different types of shapes.

27. The assembly of claim 1, wherein the environmental control material and the deformable surface are configured to conform to containers of different types of shapes while the PCM remains at its solid phase.

28. The assembly of claim 13, wherein the assembly comprises an upper part and a lower part, each part comprising the first enclosure and the second enclosure, and
the locking mechanism comprises a mechanical lock configured to form a tight sealed engagement operable to close the upper part against the lower part to establish thermal and physical contact between the upper part and the lower part.

29. The assembly of claim 1, wherein the at least one deformable surface fully physically contacts the at least one or more of the substance and the substance container.

* * * * *